(12) United States Patent
Niizeki et al.

(10) Patent No.: US 10,292,673 B2
(45) Date of Patent: May 21, 2019

(54) MEDICAL X-RAY PHOTOGRAPHING APPARATUS AND X-RAY PHOTOGRAPHING METHOD

(71) Applicant: J. MORITA MANUFACTURING CORPORATION, Kyoto-shi, Kyoto (JP)

(72) Inventors: Ryuichiro Niizeki, Kyoto (JP); Fuyuki Yamada, Kyoto (JP)

(73) Assignee: J. MORITA MANUFACTURING CORPORATION, Kyoto (JP)

(*) Notice: Subject to any disclaimer, the term of this patent is extended or adjusted under 35 U.S.C. 154(b) by 441 days.

(21) Appl. No.: 15/051,634

(22) Filed: Feb. 23, 2016

(65) Prior Publication Data
US 2016/0242728 A1 Aug. 25, 2016

(30) Foreign Application Priority Data

Feb. 25, 2015 (JP) .................. 2015-035330
Feb. 19, 2016 (JP) .................. 2016-029827

(51) Int. Cl.
*A61B 6/08* (2006.01)
*A61B 6/00* (2006.01)
(Continued)

(52) U.S. Cl.
CPC ............. *A61B 6/547* (2013.01); *A61B 6/025* (2013.01); *A61B 6/4441* (2013.01); *A61B 6/461* (2013.01);
(Continued)

(58) Field of Classification Search
CPC ....... A61B 6/025; A61B 6/032; A61B 6/4441; A61B 6/461; A61B 6/5205; A61B 6/547;
(Continued)

(56) References Cited

U.S. PATENT DOCUMENTS

| | | | |
|---|---|---|---|
| 5,553,115 A | * | 9/1996 | Odaka ................. A61B 6/08 378/170 |
| 7,023,959 B2 | | 4/2006 | Nakagawa et al. |

(Continued)

FOREIGN PATENT DOCUMENTS

| | | |
|---|---|---|
| DE | 102011004747 A1 | 8/2012 |
| DE | 102012102366 A1 | 9/2012 |
| DE | 102011082680 A1 | 3/2013 |
| JP | 2003-310595 A | 11/2003 |
| JP | 2007-029168 A | 2/2007 |
| JP | 2008-259881 A | 10/2008 |
| WO | 2009/063974 A1 | 5/2009 |

OTHER PUBLICATIONS

Extended Search Report from the corresponding European Patent Application No. 16157149.2 dated Jul. 29, 2016.

*Primary Examiner* — Irakli Kiknadze
(74) *Attorney, Agent, or Firm* — Shinjyu Global IP

(57) ABSTRACT

A medical X-ray photographing apparatus includes: a support configured to hold the X-ray generator and the X-ray detector in a facing state, the X-ray generator emitting an X-ray, the X-ray detector outputting an electric signal according to an incident X-ray; a base body that rotatably holds the support; a turning driver that turns the support about a turning axis; and a turning controller that controls the turning driver. The medical X-ray photographing apparatus also includes: a light emitter disposed at a position on a virtual loop line surrounding the turning axis; and a light emitter controller that controls the light emitter in association with the turning of the support.

21 Claims, 18 Drawing Sheets

(51) Int. Cl.
*A61B 6/02* (2006.01)
*A61B 6/03* (2006.01)

(52) U.S. Cl.
CPC .............. *A61B 6/587* (2013.01); *A61B 6/032* (2013.01); *A61B 6/5205* (2013.01)

(58) Field of Classification Search
CPC ....... A61B 6/587; A61B 6/4233; A61B 6/583; A61B 6/585; A61B 6/4291; A61B 6/542; A61B 6/484; A61B 34/20; A61B 6/4452; A61B 6/08; A61B 6/4283; A61B 6/4464; A61B 6/482; A61B 6/58; A61B 6/4208; A61B 6/4266; A61B 6/4405; A61B 6/14; A61B 6/4241; A61B 6/46; A61B 6/0492; A61B 6/501; A61N 2005/105; A61N 5/1049; G06T 2207/20164; G06T 2207/30128; G06T 2207/30188; G06T 2207/30252; G06T 7/11; G06T 7/66; G06T 7/73; H01J 1/146; H01J 61/0735; H01J 61/0737; H01J 9/42; A62B 9/06

USPC ...................................... 378/4, 19, 206, 207
See application file for complete search history.

(56) References Cited

U.S. PATENT DOCUMENTS

| | | | |
|---|---|---|---|
| 7,347,622 B2 | 3/2008 | Sadakane et al. | |
| 8,300,762 B2 | 10/2012 | Suzuki et al. | |
| 8,718,744 B2 | 5/2014 | Hannemann | |
| 9,400,416 B2 * | 7/2016 | Takahashi ............ | G03B 21/142 |
| 2003/0198317 A1 | 10/2003 | Nakagawa et al. | |
| 2004/0141590 A1* | 7/2004 | Ihalainen ................ | A61B 6/08 |
| | | | 378/206 |
| 2007/0041491 A1 | 2/2007 | Sadakane et al. | |
| 2010/0246755 A1 | 9/2010 | Suzuki et al. | |
| 2010/0322377 A1 | 12/2010 | Niizeki | |
| 2012/0039447 A1* | 2/2012 | Lalena ..................... | A61B 6/08 |
| | | | 378/206 |
| 2012/0220863 A1 | 8/2012 | Hannemann | |
| 2012/0243667 A1 | 9/2012 | Walters | |
| 2013/0253485 A1 | 9/2013 | Fehre et al. | |

* cited by examiner

US 10,292,673 B2

MEDICAL X-RAY PHOTOGRAPHING APPARATUS AND X-RAY PHOTOGRAPHING METHOD

PRIORITY

This application claims priority under 35 U.S.C. § 119 to Japanese Patent Application No. 2015-035330 filed on Feb. 25, 2015 and Japanese Patent Application No. 2016-029827 filed on Feb. 19, 2016. The entire disclosures of Japanese Patent Application No. 2015-035330 and Japanese Patent Application No. 2016-029827 are hereby incorporated herein by reference.

BACKGROUND

Field of the Invention

The present invention relates to a medical X-ray photographing technology.

Description of the Background Art

Japanese Patent Application Laid-Open No. 2003-310595 or 2008-259881 discloses a medical X-ray photographing apparatus, in which a light emission display (multi-color LED) is provided in a collimator or a cover to display the states of the medical X-ray photographing apparatus such as X-ray photography readiness, a middle of X-ray irradiation, a warning, and a failure.

An X-ray photographing apparatus in which an X-ray generator and an X-ray detector are turned around a subject is known as an apparatus that performs CT photography, tomosynthesis photography, or the like. There is a demand for the X-ray photographing apparatus configured to perform light emission display. However, in Japanese Patent Application Laid-Open No. 2003-310595 or 2008-259881, because the X-ray generator is not turned, there is no technical thought that the light emission display is performed in association with the turning. Therefore, there is a need for a technology of performing the light emission display in association with the turning.

SUMMARY

An object of the present invention is to provide a technology of performing, in an easy to understand manner, the light emission display associated with the turning of the X-ray generator and the X-ray detector.

In order to achieve the above object, a first aspect provides a medical X-ray photographing apparatus including: a support configured to turn an X-ray generator and an X-ray detector about a predetermined turning axis while holding the X-ray generator and the X-ray detector such that the X-ray generator and the X-ray detector face each other, the X-ray generator being configured to emit an X-ray, the X-ray detector being configured to output an electric signal according to an incident X-ray, a support holder configured to rotatably support the support, a turning mechanism configured to turn the support held by the support holder, a turning controller configured to control the turning mechanism, an image processor configured to generate an X-ray image by processing a plurality of projection images based on the electric signal, a light emitter disposed on a virtual loop line surrounding the turning axis, and a light emitter controller configured to control the light emitter in association with turning of the support.

Accordingly, the information about the turning of the support can be displayed to the outside in an easy to understand manner by performing the light emission display of the light emitter, which is disposed on the virtual loop line surrounding the turning axis, in association with the turning of the support.

Another aspect provides an X-ray photographing method in which X-ray photography is performed by emitting the X-ray from an X-ray generator toward an X-ray detector, the X-ray generator and the X-ray detector being supported in a facing state by a support, the X-ray photographing method including: (a) a turning controlling step of controlling turning of the support; and (b) a light-emitter controlling step of controlling a light emitter, which is disposed on a virtual loop line surrounding the turning axis, in association with the turning of the support.

Accordingly, advantageous effect similar to the medical X-ray photographing apparatus of the first aspect is obtained.

Another aspect may include a medical X-ray photographing apparatus comprising an X-ray generator, an X-ray detector, the X-ray detector emitting an electric signal in response to receiving an X-ray beam emitted from the X-ray generator, an X-ray axis upon which the X-ray beam is emitted, a support holding the X-ray generator such that it faces the X-ray detector, an image processor generating a tomosynthesis image based a processing a plurality of images, the plurality of images being associated with the electric signal, a plurality of light emitting elements, and a light controller controlling the plurality of light elements to visually display an orientation of the X-ray axis.

These and other objects, features, aspects and advantages of the present invention will become more apparent from the following detailed description of the present invention when taken in conjunction with the accompanying drawings.

DETAILED DESCRIPTION

Figure 1:
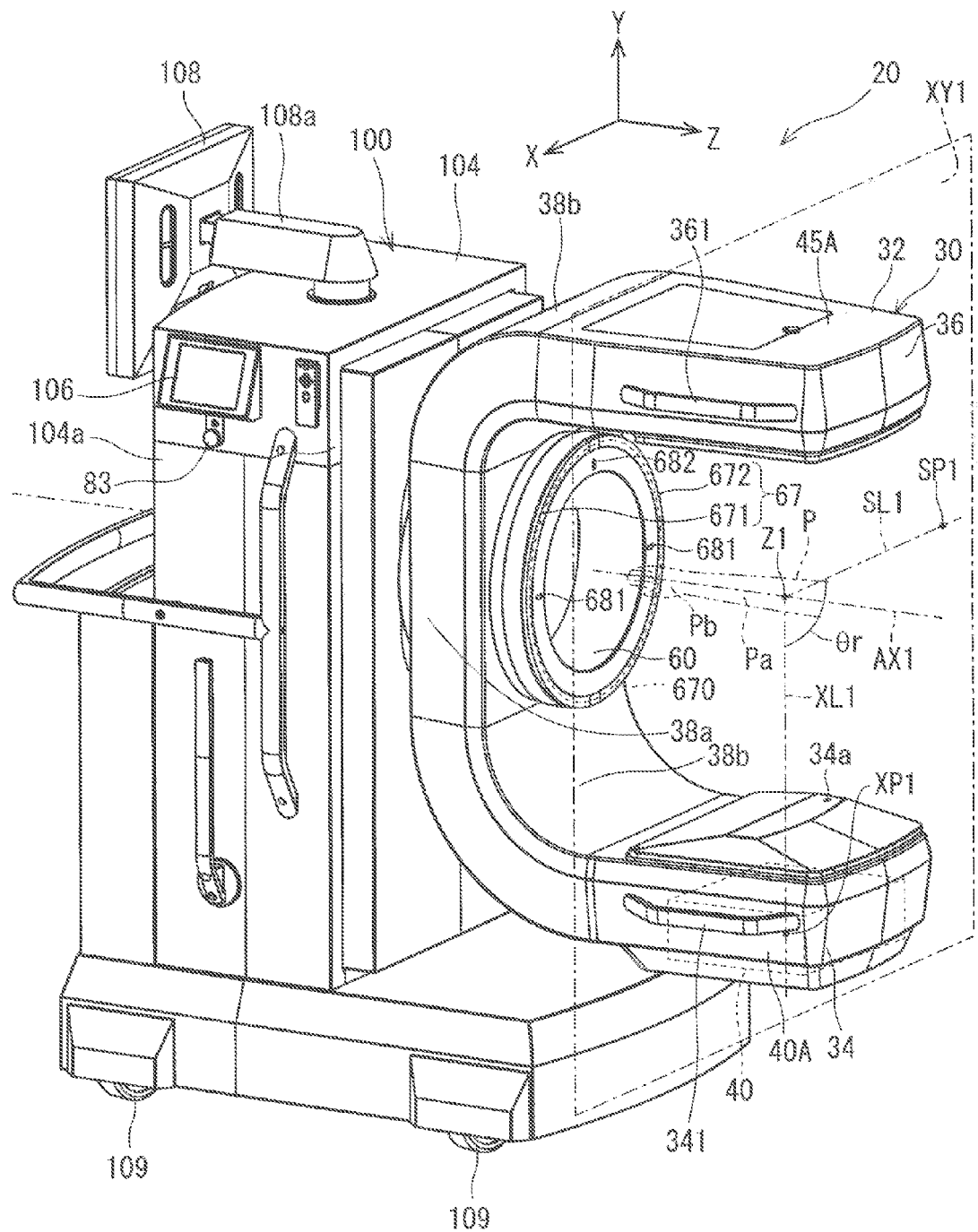
FIG. 1 is a perspective view illustrating a medical X-ray photographing apparatus according to a first preferred embodiment.

Hereinafter, preferred embodiments of the present invention will be described with reference to the accompanying drawings. The constitutional elements described in the preferred embodiments are merely illustrative, but the scope of the present invention is not intended to be limited to the preferred embodiments. In the drawings, for easy understanding, sometimes a size of each portion or the number of portions is exaggerated or simplified as needed. Through the drawings, an XYZ-rectangular coordinate system is appropriately added. A Y-direction is a direction along vertical direction (up-and-down direction), a Z-direction is a direction along a horizontal direction and a turning axis AX1, and an X-direction is a direction along the horizontal direction orthogonal to both the Y-direction and the Z-direction. Each direction is used to describe a positional relationship of each element, but not intended to limit a positional relationship between the elements.

<1. First Preferred Embodiment>

Figure 2:
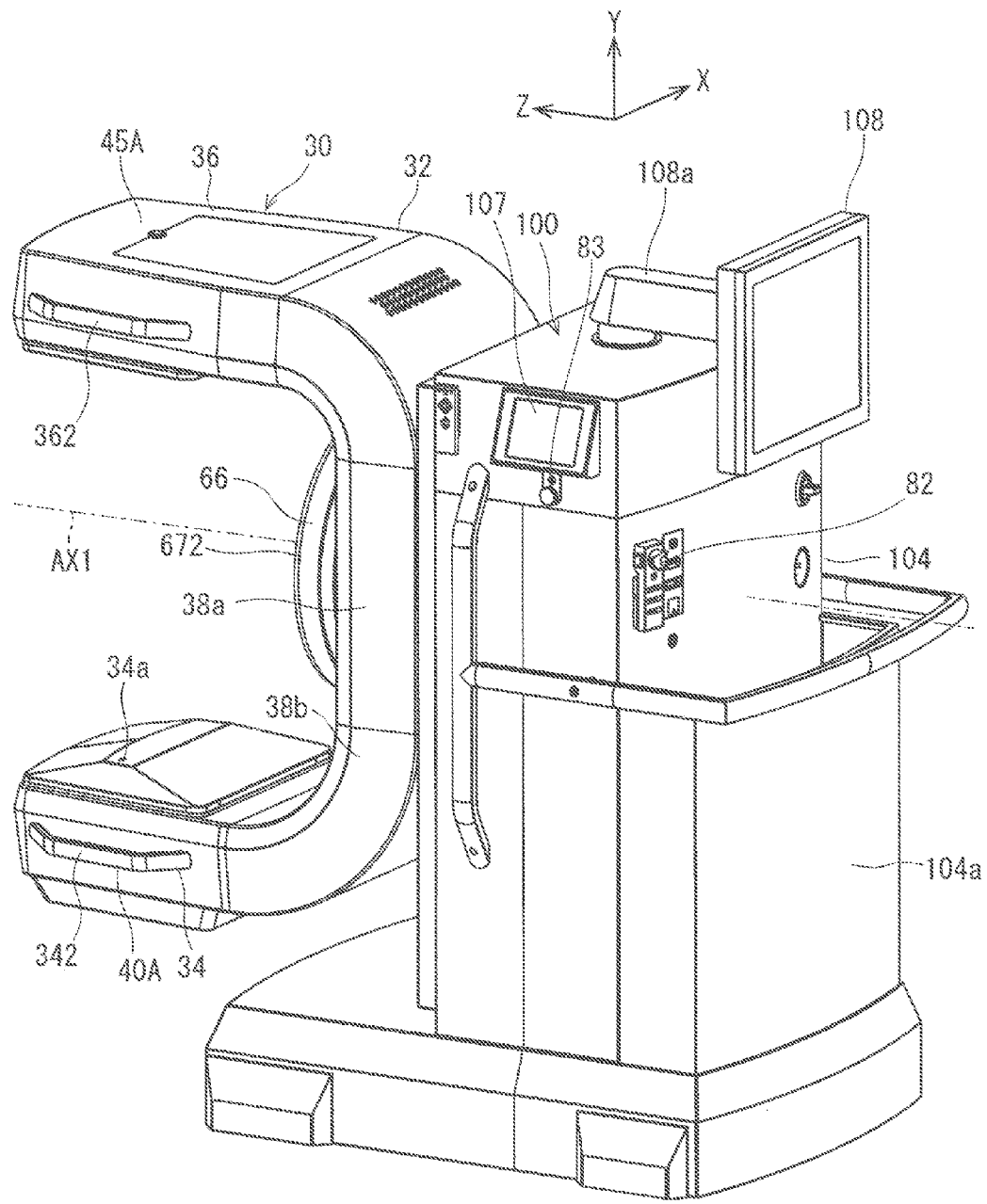
FIG. 2 is a perspective view illustrating the medical X-ray photographing apparatus of the first preferred embodiment.
Figure 3:
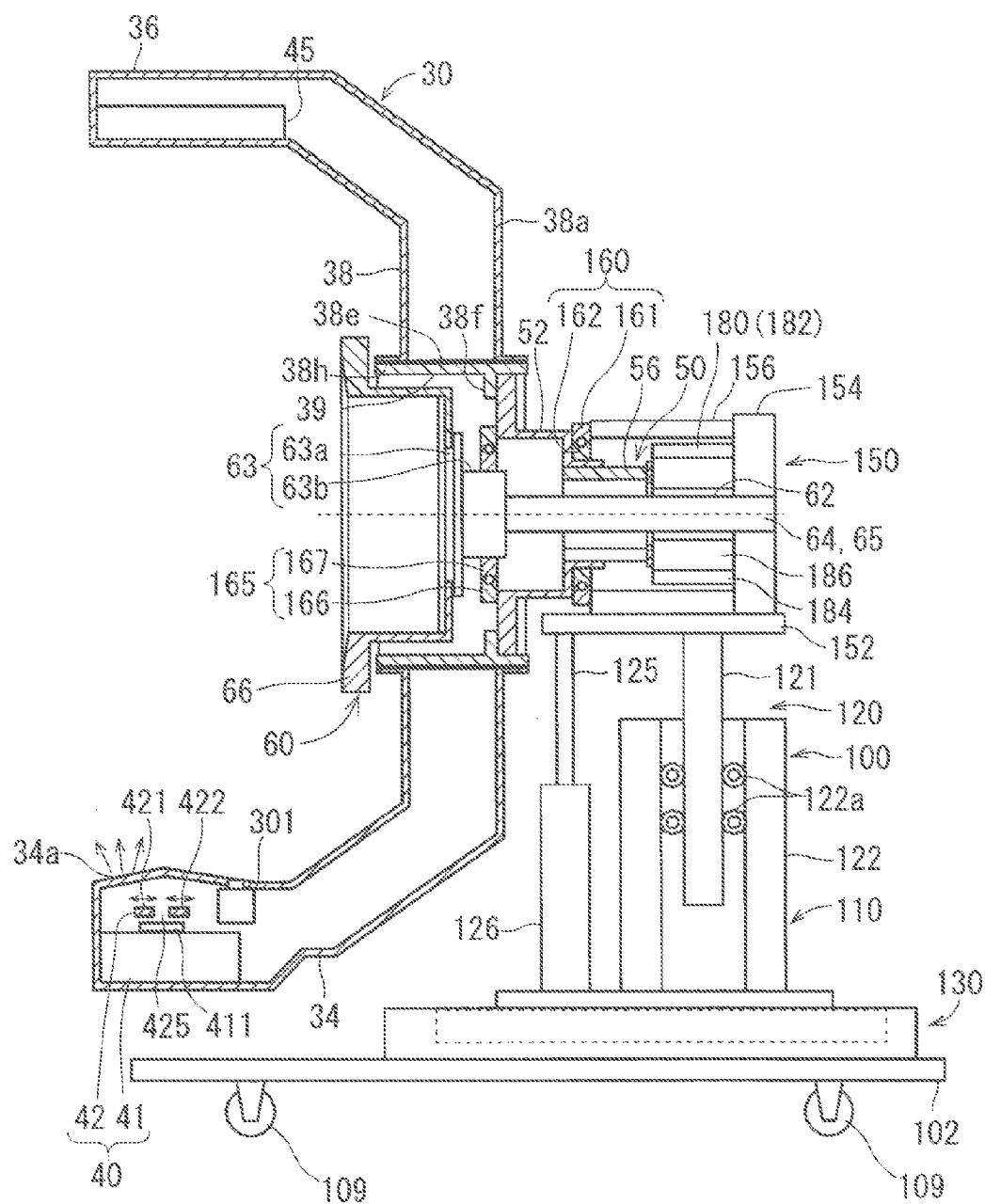
FIG. 3 is a sectional view schematically illustrating the medical X-ray photographing apparatus of the first preferred embodiment.
Figure 4:
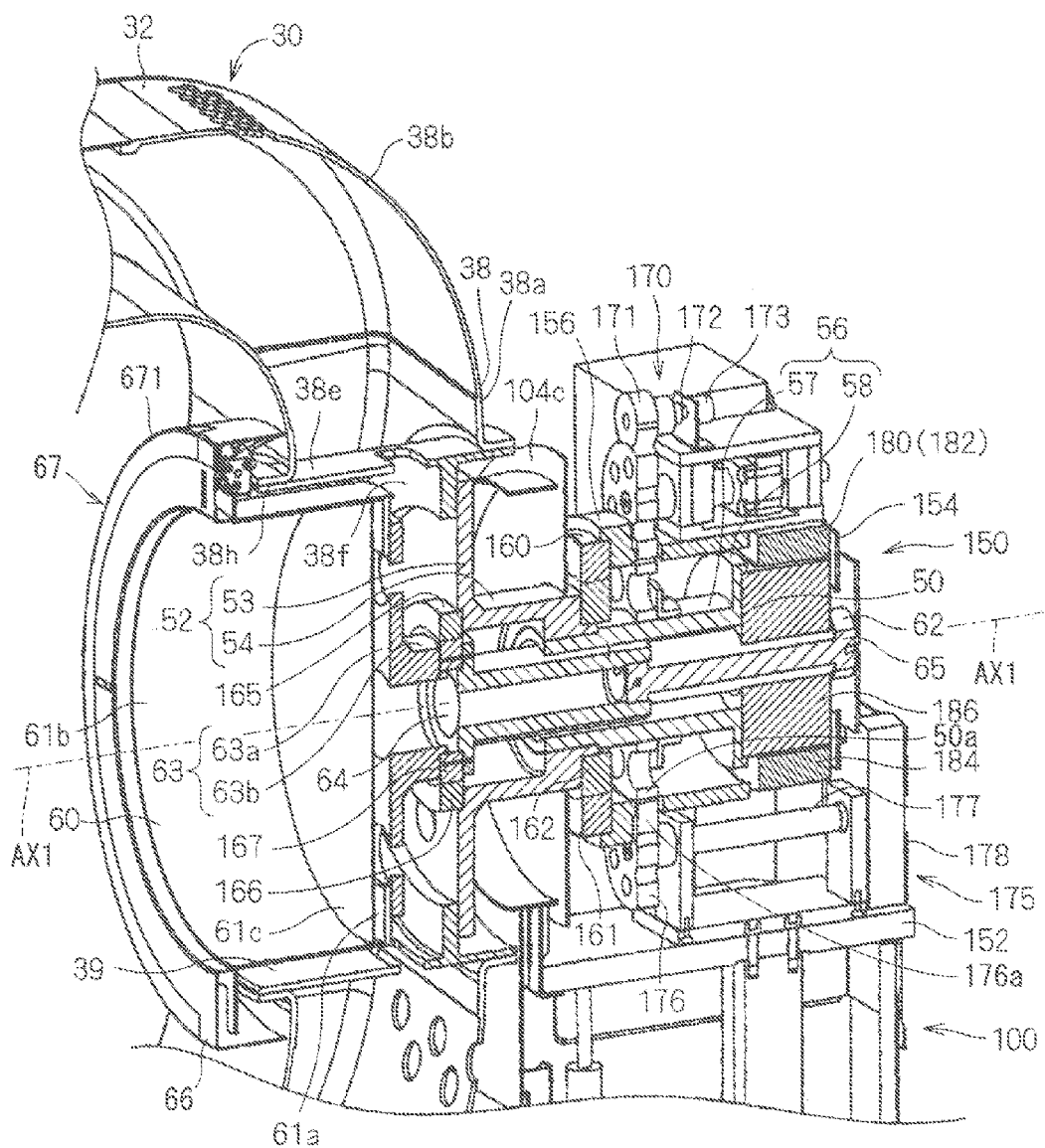
FIG. 4 is a sectional view illustrating a structural portion for supporting a support of the first preferred embodiment.
Figure 5:
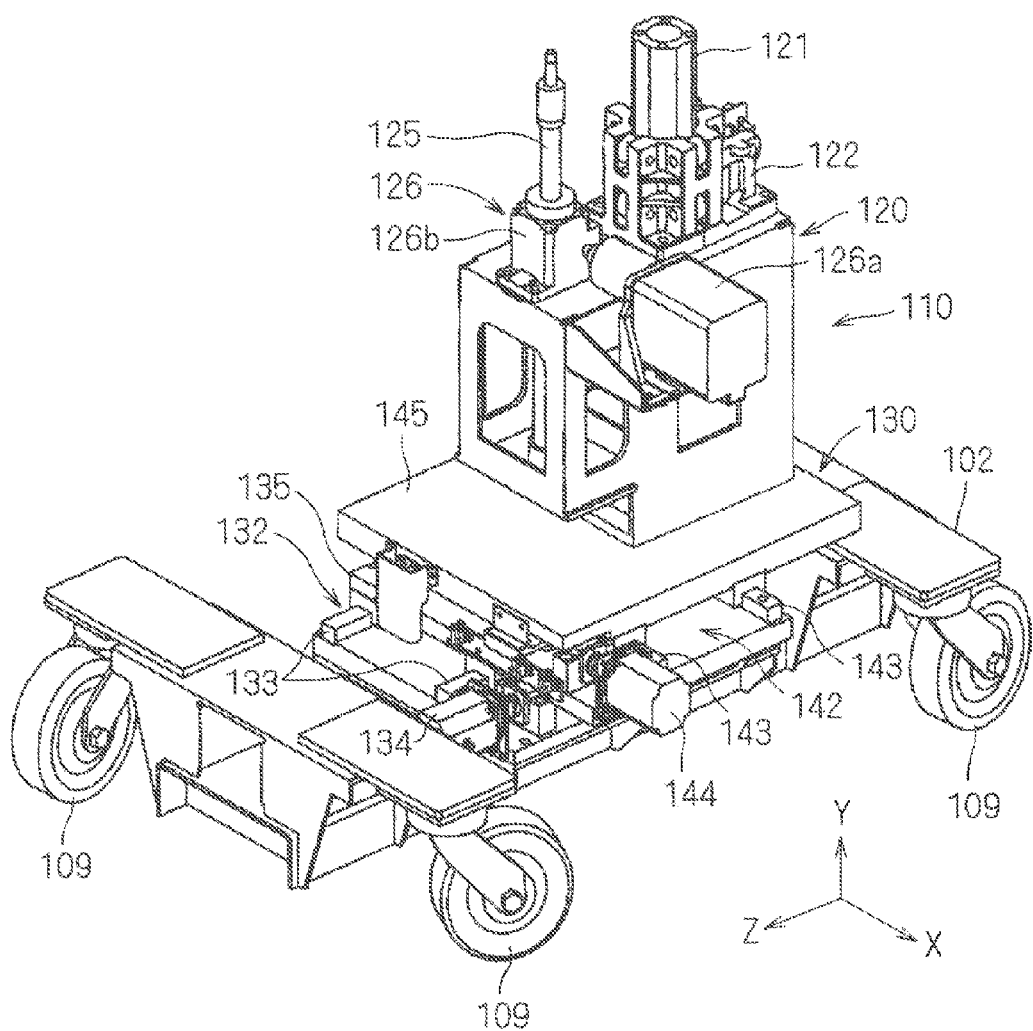
FIG. 5 is a perspective view illustrating a structural portion for moving the support of the first preferred embodiment in an XYZ-direction.

A medical X-ray photographing apparatus 20 according to a first preferred embodiment will be described. FIGS. 1 and 2 are perspective views each illustrating the medical X-ray photographing apparatus 20 of the first preferred embodiment. FIG. 1 is a view illustrating a state where the medical X-ray photographing apparatus 20 is viewed from a side of a support 30, and FIG. 2 is a view illustrating a state where the medical X-ray photographing apparatus 20 is viewed from a side of a base body 100. FIG. 3 is a sectional view schematically illustrating the medical X-ray photographing apparatus 20 of the first preferred embodiment. FIG. 4 is a sectional view illustrating a structural portion for supporting the support 30 of the first preferred embodiment. FIG. 5 is a perspective view illustrating a structural portion for moving the support 30 of the first preferred embodiment in the XYZ-direction.

The medical X-ray photographing apparatus 20 is configured to be capable of performing various kinds of medical X-ray photography such as panoramic photography and simple X-ray photography in addition to tomo synthesis photography and CT photography.

Referring to FIGS. 1 to 3, the medical X-ray photographing apparatus 20 is suitable for the X-ray photography of a part of a patient as a subject P, for example, a mouth cavity area including teeth and a jaw, a head including an otorhinolaryngology area, a cervical vertebrae, an arm joint, a finger, a breast, a lumbar vertebrae, a hip joint, a knee, and a leg. The medical X-ray photographing apparatus 20 includes an X-ray generator 40, an X-ray detector 45, the support 30, and the base body 100.

The X-ray generator 40 is configured to be capable of emitting an X-ray cone beam. The X-ray detector 45 detects the X-ray, which is transmitted through the subject P of a photographing target irradiated with the X-ray emitted from the X-ray generator 40.

For example, the support 30 includes an exterior part 32 made of carbon fiber reinforced plastic. The support 30 is configured to support the X-ray generator 40 and the X-ray detector 45 while the X-ray generator 40 and the X-ray detector 45 face each other by the exterior part 32.

The base body 100 is a base in which each part constituting the medical X-ray photographing apparatus 20 is directly or indirectly assembled. Particularly, the base body 100 turnably supports the support 30 such that the X-ray generator 40 and the X-ray detector 45 turn about the turning axis AX1. Hereinafter, for convenience, a side on which the support 30 is provided is referred to as a front side with respect to the base body 100, and a side opposite to the front side is referred to as a rear side.

In the first preferred embodiment, the base body 100 supports the support 30 such that the turning axis AX1 is provided along the horizontal direction. Therefore, the X-ray generator 40 and X-ray detector 45, which are supported by the support 30, are disposed while facing each other with a gap across the turning axis AX1 along the horizontal direction orthogonal to the vertical direction. The X-ray generator 40 and X-ray detector 45 turn about the turning axis AX1.

Although the turning axis AX1 is horizontally disposed, the turning axis AX1 is not exactly disposed in the horizontal direction. For example, it is assumed that Szx (not illustrated) is a horizontally-spread two-dimensional plane, that Da (not illustrated) is an axial direction of the turning axis AX1, and that Aa (not illustrated) is a minimum angle formed between the axial direction Da and the two-dimensional plane Szx. Although desirably the angle Aa is zero, the angle Aa may range from +20° to −20°. Although not illustrated, the turning axis AX1 can mechanically be tilted such that the angle Aa temporarily becomes zero. In this case, the horizontal disposition is also adopted.

In the medical X-ray photographing apparatus 20, the X-ray photography of the subject P is performed as follows. Specifically, the subject P is disposed between the X-ray generator 40 and the X-ray detector 45 along the turning axis AX1 from the opposite side to the base body 100. At this point, the support 30 rotates about the turning axis AX1, whereby the X-ray generator 40 and the X-ray detector 45 rotate about the turning axis AX1. Based on an electric signal output from the X-ray detector 45 according to intensity of the X-ray, calculation processing of reconstructing the X-ray image of the subject P is performed to generate the X-ray image of the subject P.

Therefore, the medical X-ray photographing apparatus 20 is configured as an apparatus that suitably performs X-ray CT photography while the subject P is disposed along the horizontal direction. However, the support may be supported so as to be turnable about the turning axis tilted with respect to the horizontal direction or the turning axis along the vertical direction.

<Support 30>

The support 30 includes the exterior part 32. The exterior part 32 is a support element that incorporates and supports the X-ray generator 40 and the X-ray detector 45 in the facing state. The exterior part 32 can constitute an element that covers and protects the X-ray generator 40, the X-ray detector 45, and a wiring member and a control board thereof.

The exterior part 32 is made of carbon fiber reinforced plastic (CFRP). The carbon fiber reinforced plastic is light compared with a metallic material such as iron, and has excellent strength. The exterior part 32 incorporates and supports the X-ray generator 40 and the X-ray detector 45, which allows weight reduction of the support 30 including the exterior part 32. The weight reduction of the support 30 enables the weight reduction of a component (to be described later) that rotatably supports the support 30. Therefore, the weight reduction of the whole medical X-ray photographing apparatus 20 can be achieved.

There are various ways how to form the exterior part 32 using the carbon fiber reinforced plastic. The exterior part 32 may be formed by bonding woven carbon fiber to plastic, or the exterior part 32 may be formed by uniformly dispersing and mixing finely-cut carbon fiber in plastic.

The component for supporting the X-ray generator 40 and the X-ray detector 45 is made of the carbon fiber reinforced plastic having excellent rigidity, the component is formed into the exterior part 32, and a sectional shape is formed into a cyclic shape (preferably, a box shape) in a plane orthogonal to an extending direction of the exterior part 32, thereby ensuring the configuration having the excellent rigidity. Thus, the weight reduction and high rigidity of the support 30 including the exterior part 32 can reduce a bending deformation of the support 30 during the turning of the support 30. As a result, the X-ray generator 40 and the X-ray detector 45 can accurately be held during the turning, and the weight reduction of the medical X-ray photographing apparatus 20 can be achieved. Particularly, the X-ray generator 40 and the X-ray detector 45 are prevented from shifting due to the bending deformation of a support structural portion thereof, whereby a position shift can be prevented between images sequentially obtained during the turning of the X-ray generator 40 and the X-ray detector 45. As a result, a high-accuracy X-ray CT image can be obtained.

Specifically, the exterior part 32 includes a pair of arms 34 and 36 extending along the turning axis AX1 and an arm base 38. The arm 34 constitutes an X-ray generation part 40A of the support 30 together with the X-ray generator 40 (to be described later), and the arm 36 constitutes an X-ray detection part 45A of the support 30 together with the X-ray detector 45 (to be described later).

The pair of arms 34 and 36 is formed into a square pipe shape in which a leading end portion is closed, and the pair of arms 34 and 36 is disposed so as to extend along the turning axis AX1.

The arm base 38 includes a middle trunk part 38a and bent parts 38b at both end portions of the middle trunk part 38a. The middle trunk part 38a is formed into a square pipe shape extending in a direction orthogonal to the turning axis AX1, and the bent part 38b is formed into a square pipe shape that is bent from direction orthogonal to the turning axis AX1 to a direction along the turning axis AX1 at an end portion of the middle trunk part 38a. The middle trunk part 38a and the bent parts 38b at both the end portions of the middle trunk part 38a are connected to each other so as to form one square pipe as a whole.

The pair of arms 34 and 36 is connected to both end portions of the arm base 38, and supported in parallel by the arm base 38 in the facing state across the turning axis AX1.

In the exterior part 32, the pair of arms 34 and 36 and the arm base 38 are formed into a continuous pipe shape (in this case, the square pipe shape) so as to constitute U-shape as a whole. In the exterior part 32, a cavity is formed from an end portion of the arm 34 to an end portion of the arm 36 through the arm base 38. For example, coating may be applied to a surface of the exterior part 32.

<Grips 341, 342, 361, and 362>

In the support 30, grips 341, 342, 361, and 362 are provided on both sides of the leading end portions of the pair of arms 34 and 36. As described later, when an electromagnetic brake of a brake 178 in FIG. 4 is released, the support 30 can manually be turned about the turning axis AX1. During the manual operation, an operator pulls or pushes the arm 34 or the arm 36 while gripping the grips 341 and 342 or the grips 361 and 362, which allows the easy turning of the support 30.

<X-Ray Generator 40 and X-Ray Detector 45>

The X-ray generator 40 is attached to the leading end portion of the arm 34, and the X-ray detector 45 is attached to the leading end portion of the arm 36.

The X-ray generator 40 includes an X-ray generating body 41 and an X-ray regulator 42. The X-ray generating body 41 includes an X-ray tube constituting an X-ray source, and is configured to emit the X-ray. The X-ray regulator 42 is provided in front of the X-ray generating body 41 in an X-ray irradiation direction, and regulates the X-ray irradiation area. The X-ray regulator 42 is formed of a plate-like member made of an X-ray shielding material, which makes an opening regulating spread of the X-ray, and sometimes called a collimeter. The opening is formed into a substantially square shape having a predetermined size according to a mode of the X-ray CT photography or the tomosynthesis photography. Depending on the mode of the X-ray photography, the opening may be formed into a slit shape such that the subject can be scanned. Various configurations are adopted in the plate-like member used to make the opening according to a target area of the X-ray photography or CT photography. Examples of the plate-like members include a plate-like member in which one or a plurality of openings are provided in one X-ray shielding plate, a plate-like member in which at least two plates are overlapped and deviated from each other to make the opening, and a plate-like member in which the opening shape and opening area can be changed by movably disposing at least two plates. For example, the X-ray is regulated by the opening so as to become the X-ray cone beam.

In the example of FIG. 3, a plurality of shielding plates 421 and 422 forms an opening 425 permitting passage of the X-ray. The shielding plates 421 and 422 are independently displaced in the Z-direction with respect to the X-ray generating body 41. The plurality of shielding plates 421 and 422 are brought close to each other to decrease a width in the Z-direction of the opening 425, and the plurality of shielding plates 421 and 422 are separated from each other to increase the width in the Z-direction of the opening 425. An X-ray irradiation direction can be changed with respect to the Z-direction by displacing the shielding plates 421 and 422 in the identical direction, and the shielding plates 421 and 422 can be moved such that both the irradiation direction and the width are changed. Although the shielding plates 421 and 422 are displaced by a shielding plate driving mechanism including an actuator such as a motor, the illustration of the shielding plate driving mechanism is omitted.

Whereas the plurality of shielding plates 421 and 422 are a member that regulates the passage of the X-ray in a longitudinal direction, and a plurality of crosswise shielding plates (not illustrated) that regulate the passage of the X-ray in a crosswise direction are also provide. The plurality of crosswise shielding plates are disposed adjacently in front or at the back of the shielding plates 421 and 422 in the X-ray irradiation direction, and regulate the X-ray generated from the output port 411 of the X-ray generating body 41 in the crosswise direction intersecting the moving directions of the shielding plates 421 and 422. The independent displacements of the plurality of crosswise shielding plates in the direction intersecting the Z-direction with respect to the X-ray generating body 41 are similar to the displacements of the shielding plates 421 and 422 except the direction. Therefore, the description of the displacements of the plurality of crosswise shielding plates is omitted.

The X-ray generator 40 is attached to the leading end portion of the arm 34 with the position and attitude in which the X-ray cone beam can be emitted toward the leading end portion of the arm 36.

The X-ray detector 45 is formed of a flat panel deflector (FPD) or an X-ray Image Intensifier (I.I.), which includes a two-dimensionally-spread detection surface.

The X-ray detector 45 is attached to an inward portion of the leading end portion of the arm 36 in the attitude in which the detection surface can be irradiated with X-ray from the X-ray generator 40.

The X-ray generator 40 and the X-ray detector 45 are supported by the pair of arms 34 and 36 in the facing state across the turning axis AX1. The X-ray cone beam is emitted from the X-ray generating body 41 toward the X-ray detector 45 while the spread of the X-ray cone beam is regulated by the X-ray regulator 42. The X-ray cone beam arrives at the detection surface of the X-ray detector 45 through the turning axis AX1 and surroundings thereof.

The wiring for the X-ray generator 40 and X-ray detector 45 is provided through a space in the exterior part 32. An opening for attaching work of the wiring or control board or an opening for heat radiation may be made at an appropriate position of the exterior part 32.

A positioning light irradiation part 34a for outputting positioning light is provided in the leading end portion of the arm 34. The positioning light irradiation part 34a is formed of a light emitting diode or an electric bulb so as to emit visible light. The positioning light irradiation part 34a is attached to the leading end portion of the arm 34 in the attitude in which the light is output toward a space between the X-ray generator 40 and the X-ray detector 45. The visible light output from the positioning light irradiation part 34a is regulated by a shielding plate in which a slit is formed and a lens so as to indicate a photographing position of the X-ray generator 40 and the X-ray detector 45. Here, examples of a mode in which the photographing position is indicated by the visible light output from the positioning light irradiation part 34a include the case where the visible light is aimed at the turning axis AX1 and the case where the visible light indicates a boundary of the photographing area. Moreover, the visible light may be output in a linear, point, or planar form. An attaching position of the positioning light irradiation part 34a is not limited to the leading end portion of the arm 34, but the positioning light irradiation part 34a may be attached to another portion of the arm 34 or the arm 36.

<Turning Support Shaft 50>

The support 30 includes a turning support shaft 50 provided so as to extend onto the opposite side to the X-ray generator 40 and X-ray detector 45 along the turning axis AX1.

As illustrated in FIG. 3, a cavity 39 is formed in an arm base 38 along the turning axis AX1. Openings 38h opened around the turning axis AX1 are formed in front and rear portions of a middle portion in the extending direction of the arm base 38. A pipe member 38e is fitted in the opening 38h, and fixed to the exterior part 32 by a screw or the like. The cavity 39 is formed on an inner circumference side of the pipe member 38e, and forms a cylindrical space spreading around the turning axis AX1. A fixing guard 38f projecting toward the inner circumference side extends in an inner circumference of the pipe member 38e and in the middle portion in the direction of the turning axis AX1.

The turning support shaft 50 includes a first turning support shaft 52 and a second turning support shaft 56.

As illustrated in FIG. 4, the first turning support shaft 52 includes a disc part 53 in which the center is opened and a pipe shape part 54 that extends from the center opening of the disc part 53 toward one of main surface sides (rear side) of the disc part 53. The first turning support shaft 52 is formed into a hollow shape in which the center opening of the disc part 53 and a space of the pipe shape part 54 are continuously provided.

The second turning support shaft 56 includes a pipe shape part 57 and a fixing guard 58 that spreads toward an outer circumference side from one end portion (rear-side end) of the pipe shape part 57.

The other end portion (front-side end portion) of the pipe shape part 57 is coupled to one end portion (rear-side end portion) of the pipe shape part 54 of the first turning support shaft 52. At this point, the other end portion of the pipe shape part 57 is fitted in one end portion of pipe shape part 54, whereby the pipe shape part 57 and the pipe shape part 54 are coupled to each other. The fixing guard 58 is coupled to a hollow rotation shaft 186 of a turning driver 180 (to be described later).

The disc part 53 is screwed while overlapping the pipe fixing guard 38f of the pipe member 38e, whereby the turning support shaft 50 is fixed to the exterior part 32. In this fixed state, the turning support shaft 50 extends to the opposite side to the pair of arms 34 and 36 along the turning axis AX1 with respect to the exterior part 32. The turning support shaft 50 is formed into a hollow shape in which an inner space of the first turning support shaft 52 and an inner space of the second turning support shaft 56 are continuously provided as a whole.

The turning support shaft 50 is rotatably supported by a first bearing 160 and a second bearing 165 (to be described later), whereby the support 30 is rotatably supported about turning axis AX1 in a cantilever state. The other end portion of turning support shaft 50 is relatively unrotatably coupled to the hollow rotation shaft 186 of the turning driver 180, and the other end portion is driven and rotated by the turning driver 180, whereby the support 30 is driven and rotated about the turning axis AX1. When the support 30 is rotated about the turning axis AX1, the X-ray generator 40 and the X-ray detector 45 rotate about the turning axis AX1, which allows the acquisition of a plurality of X-ray projection data pieces in which an affected area is photographed from a plurality of directions necessary to reconstruct the CT image.

An accommodation part 60 is provided in the cavity 39. The accommodation part 60 is formed into a cylindrical shape with a bottom, and configured to be capable of accommodating at least a part of the subject P. More specifically, in the accommodation part 60, a circumferential wall 61*b* is formed around a disc part 61*a*. The opening is made in a central portion of the disc part 61*a*. A bottom plate 61*c* is attached in the accommodation part 60 so as to close the opening of the disc part 61*a*. It is only necessary to dispose at least a part of the accommodation part 60 in the cavity 39. Accordingly, a depth side or front side of the accommodation part 60 may project from the cavity 39.

A part (for example, a hand pb) can be accommodated in the accommodation part 60 while the subject P (particularly, a part of the patient, and a portion constituting an X-ray photography target, for example, an upper arm Pa) is disposed between the X-ray generator 40 and the X-ray detector 45.

Although the accommodation part 60 is accommodated in the cavity 39, but the accommodation part 60 is not fixed to the pipe member 38*e*. A center axis of the accommodation part 60 is aligned with the turning axis AX1, and the accommodation part 60 is unrotatably supported by an accommodation part support 62 while being open toward the space between the pair of arms 34 and 36.

The accommodation part support 62 includes an attaching part 63, a first accommodation part supporting shaft 64, and a second accommodation part supporting shaft 65.

The attaching part 63 includes a disc part 63*a* that is open at the center thereof and a pipe shape part 63*b* that extends from the center opening of the disc part 63*a* toward one of main surface sides (rear side) of the disc part 63*a*.

The first accommodation part supporting shaft 64 is formed into a cylindrical shape. One end portion (front-side end portion) of the first accommodation part supporting shaft 64 is coupled to the end portion of the pipe shape part 63*b*. At this point, one end portion (front-side end portion) of the first accommodation part supporting shaft 64 is coupled to the end portion of the pipe shape part 63*b* with an inside cyclic member 167 of the second bearing 165 (to be described later) interposed therebetween.

The second accommodation part supporting shaft 65 is formed into a round rod shape. One end portion (front-side end portion) of the second accommodation part supporting shaft 65 is coupled to the other end portion (rear-side end portion) of the first accommodation part supporting shaft 64. At this point, one end portion (front-side end portion) of the second accommodation part supporting shaft 65 is coupled to the other end portion (rear-side end portion) of the first accommodation part supporting shaft 64.

One end portion (front-side end portion) of the accommodation part support 62 is fixed to an outward surface of the disc part 61*a* of the accommodation part 60, the accommodation part support 62 is supported in the attitude in which the accommodation part support 62 extends along the turning axis AX1 toward the opposite side to the opening of the accommodation part 60 with respect to the accommodation part 60. The accommodation part support 62 is relatively rotatably provided in the turning support shaft 50 through the inner space of the turning support shaft 50 and the inner space of the hollow rotation shaft 186 of the turning driver 180. The other end portion (rear-side end portion) of the accommodation part support 62 is projected outward from the hollow rotation shaft 186, and is fixed to a turning support base 150 (to be described later), which allows the accommodation part 60 to be unrotatably supported at a constant position and attitude in the cavity 39.

Preferably, the cavity 39 has the opening shape as large as possible in a range in which a supporting function of the exterior part 32 is maintained. Preferably, the opening of the accommodation part 60 is made as large as possible in a range in which the accommodation part 60 can be accommodated in the cavity 39.

In this case, the accommodation part 60 is unrotatably supported. Alternatively, the accommodation part 60 may be rotatably supported. In this case, even if the support is rotated while the accommodation part is relatively rotatably supported in the support, preferably the accommodation part is not driven by the rotation of the support, namely, the accommodation part remains in the unrotatable state.

<Light Emitter 67>

In the accommodation part 60, the portion projecting toward the outside of the cavity 39 constitutes a ring 66 that is formed into a cyclic shape around the turning axis AX1. A light emitter 67 is provided in a front surface (+Z-side surface) of the ring 66. The light emitter 67 is disposed along a virtual loop line 670 around the turning axis AX1. In the first preferred embodiment, the light emitter 67 is disposed into a substantial cyclic shape along an end edge of the ring 66.

The virtual loop line 670 is a line that is assumed to be around the turning axis AX1 around which the light emitting element of the light emitter 67 is disposed. The virtual loop line 670 is an indication line so as to indicate the angle of the support 30 (to be described later) when the light emitting element of the light emitter 67 is disposed, and virtual loop line 670 is a line that is fixed around the turning axis AX1 in designing. Therefore, the virtual loop line 670 is not always drawn as an actual line in the medical X-ray photographing apparatus 20. In this sense, the term "virtual" is used.

The light emitting element disposed on the virtual loop line only has to perform functions of light emission display of the center direction and light emission display of the turning range (to be described later), and thus does not have to occupy the entire virtual loop line without a gap and may have an intermittent portion.

The light emitter 67 includes two arc light emitting elements 671 and 672 that emit the light at positions separated from each other. For example, the light emitting elements 671 and 672 are formed of many color LEDs, and light emission of each color LED is controlled by a light emitter controller 715 (to be described later). Alternatively, the light emitting elements 671 and 672 may be formed of the LED or electric bulb that emits the monochromatic visible light. The light emitter 67 may be formed of a liquid crystal display, and preferably the light emitter 67 may be formed of a color liquid crystal display.

The light emitting elements 671 and 672 are the two arc light emitting elements, but, if the light emitting elements 671 and 672 are each a collection of LEDs or the like, for example, each LED or the like can be considered as a fragmented light emitting element. Similarly, if the light emitting elements 671 and 672 are each formed of a liquid crystal display, each pixel of the liquid crystal display can be considered as a further fragmented light emitting element.

In the illustrated example, on the virtual loop line 670, the light emitting element of the light emitter 67 is divided into the left (+X) light emitting element 671 and the right (−X) light emitting element 672 arranged to form arcs, and the light emitter 67 has narrow portions in which there are no light emitting elements between the left light emitting element 671 and the right light emitting element 672 at the top and the bottom thereof. However, a light emitting element 671A (not illustrated) disposed on the entire virtual loop line 670 without a gap may be provided.

In either case, the light emitter 67 has a closed circular shape.

In a case where the light emitting elements 671, 672, and 671A include LEDs of a plurality of colors, for example, the LEDs may sequentially be arranged such that a set of red, blue, and green LEDs disposed close to each other at one position and another set of red, blue, and green LEDs similarly disposed close to each other at another position are arranged at regular intervals, or the same array pattern may be repeated at equal intervals such that red, blue, green, red, blue, green, . . . LEDs are arranged in this order.

In the first preferred embodiment, the light emitting elements 671 and 672 constitute a corner portion from the front surface to the outer circumferential surface of the ring 66. For this reason, as illustrated in FIG. 1, a light emission state of the light emitter 67 can visually be recognized from the direction along the turning axis AX1, and also recognized from a radial direction orthogonal to the turning axis AX1. Thus, the operator can easily visually recognize the light emission state of the light emitter 67 from a lateral position of the base body 100 or a position on the side of the support 30. As described later, the light emitter controller 715 controls the light emitting elements 671 and 672 in association with the turning of the support 30. Therefore, the light emitting elements 671 and 672 are provided so as to be easily visually recognized, so that an operating state of the medical X-ray photographing apparatus 20 can easily be checked.

The light emitting elements 671, 672, and 671A may be embedded in the front surface of the ring 66 so as to be visually recognized from the direction along the turning axis AX1 but not to be visually recognized from the radial direction orthogonal to the turning axis AX1, or may be embedded in the outer circumferential surface of the ring 66 so as to be visually recognized from the radial direction orthogonal to the turning axis AX1 but not to be visually recognized from the direction along the turning axis AX1.

The light emitter 67 disposed on the virtual loop line 670 surrounding the turning axis AX1 performs the light emission display in association with the turning, so that information about the turning can be displayed so as to be easily known from the outside. The light emission display of the information about the turning of the support 30 can be performed in an intuitive and easy to understand manner by disposing the light emitter 67 on the circumference of a circle with the turning axis AX1 as the center.

<Visible Beam Emitters 681 and 682>

Positioning visible beam emitters 681 and 682 are provided in the front surface (+Z-side surface) of the ring 66. As illustrated in FIG. 1 and the like, each visible beam emitter 681 is provided on a +X-side portion and a −X-side portion of the ring 66, and the visible beam emitter 682 is provided in a +Y-side portion. The visible beam emitters 681 and 682 are provided inside the light emitter 67.

The visible beam emitters 681 and 682 are formed of the light emitting diode or electric bulb so as to emit the visible beam. The position of the subject P relative to the support 30 is displayed by irradiating the subject P with the visible beams emitted from the visible beam emitters 681 and 682. Therefore, the position irradiated with the X-ray can be displayed on the subject P. The X-ray irradiation position is easily checked, so that the subject P can correctly be positioned.

There is no particular limitation to the shapes of the beams emitted from the visible beam emitters 681 and 682. For example, the beam may be formed into a linear, point, or planar shape.

In the support 30 of the first preferred embodiment, the turning support shaft 50 extending in the Z-direction is coupled to the arm base 38, and the arms 34 and 36 extend from the arm base 38 in the Z-direction opposite to the direction in which the turning support shaft 50 extends. This arrangement allows the space where the subject P is positioned to be formed between the arms 34 and 36.

The support 30 is formed into a U-shape as a whole for the purpose of the simplification and weight reduction of the support 30. The U-shape does not exactly become the shape of a character "U", but the support 30 may be formed into a C-shape or a shape in which the pair of arms extend in parallel in a right angle with respect to both the end portions of the arm base. That is, the support 30 includes the arm base 38 and the arms 34 and 36, the arm base 38 extends substantially in the direction orthogonal to the Z-direction although the arm base 38 may be formed in either a linear shape or a curved shape, the arms 34 and 36 extend substantially along the Y-direction although the arms 34 and 36 may be formed in either the linear shape or the curved shape, and the arm base 38 and the arms 34 and 36 may smoothly be connected while curved or connected with a clear angle. The shape obtained by forming the arm base 38 and the arms 34 and 36 in this manner is generically called the U-shape.

<Base Body 100>

As illustrated in FIGS. 1 to 5, the base body 100 is a portion that supports the support 30 and the accommodation part 60. The base body 100 includes a seating 102, an XYZ-direction moving mechanism 110, and a turning support base 150.

The seating 102 is a portion that constitutes a base provided in a lower portion of the medical X-ray photographing apparatus 20. The seating 102 has a stretch to a degree to which the medical X-ray photographing apparatus 20 can be supported in a constant attitude so as not to be tilted in planar view. The seating 102 may have a structure in which a plurality of frames are combined, or a plate-like structure.

Wheels 109 are provided below the seating 102 as a rolling element that rolls on a floor. At this point, the wheels 109 are provided at four corners below the seating 102. When the operator pushes the medical X-ray photographing apparatus 20, the medical X-ray photographing apparatus 20 can move on the floor and the like.

The medical X-ray photographing apparatus 20 can easily be moved by providing the wheels 109. The provision of the wheels 109 and the weight reduction of the support 30 are combined to enable the easier movement of the medical X-ray photographing apparatus 20.

A known lock mechanism that stops the rolling of the wheel may be provided in at least a part of the wheels to maintain the stopping state of the medical X-ray photographing apparatus 20.

The XYZ-direction moving mechanism 110 is provided on the seating 102. The XYZ-direction moving mechanism 110 moves each part (including the support 30), which is directly or indirectly supported by the turning support base 150 and the turning support base 150, in the Z-direction parallel to the turning axis AX1, the X-direction orthogonal to the Z-direction in the horizontal plane, and the Y-direction that is the vertical direction orthogonal to both the Z-direction and the X-direction with respect to the seating 102.

The turning support base 150 is supported by the XYZ-direction moving mechanism 110 so as to be movable in the XYZ-direction. The turning support base 150 is configured to be capable of supporting the turning support shaft 50 and the accommodation part support 62.

The support 30 is supported by the turning support base 150, whereby the support 30 is supported so as to be movable in the XYZ-direction together with the turning support base 150. The accommodation part 60 is also directly or indirectly supported by the turning support base 150, whereby the accommodation part 60 is supported so as to be movable in the XYZ-direction together with the support 30.

The base body 100 includes a cover 104 that covers each part. The cover 104 is made of resin or metal, and the cover 104 protects each part such that the part is not exposed to the outside.

The cover 104 includes a cover body 104a and a front cover 104b. The cover body 104a covers the top and surroundings of the XYZ-direction moving mechanism 110, and is fixed at a constant position with respect to the seating 102. In the cover body 104a, an opening is made in a portion corresponding to the support 30, and the front cover 104b is provided so as to close the opening. Although not illustrated, the front cover 104b is fixed to a Z-direction moving plate that moves in the Z-direction in the XYZ-direction moving mechanism 110, and the front cover 104b closes the opening of the cover body 104a while moving only in the Z-direction together with the Z-direction moving plate.

An opening in which the turning support shaft 50 is inserted is made in the front cover 104b. In the turning support shaft 50, a shaft cover 104c is attached around a portion that passes through the front cover 104b. A base plate 152 is fixed to the shaft cover 104c. The opening is made in the center of the shaft cover 104c, and the turning support shaft 50 passes through the opening. Because the shaft cover 104c is mechanically separated from the turning support shaft 50, the shaft cover 104c is not rotated by following the turning support shaft 50. Through the fixing relationship, the shaft cover 104c moves in the Z-direction together with the front cover 104b, and the shaft cover 104c can close the opening made in the front cover 104b while moving in the X-direction and Y-direction with respect to the front cover 104b.

Display operation panels 106 and 107 are provided on both sides in an upper portion of the base body 100. For example, the display operation panels 106 and 107 are formed of touch panels. The display operation panels 106 and 107 are used as a display device that displays various pieces of information about the X-ray photography and an input device that is used to input various instructions associated with the X-ray photography. As a matter of course, the display device and the input device may separately be incorporated. The display operation panels 106 and 107 are provided on both the sides of the base body 100 (support holder), respectively, which allows the medical X-ray photographing apparatus 20 to be operated on either side of the base body 100. Therefore, the freedom degree of disposition of the medical X-ray photographing apparatus 20 can be improved.

An image displaying monitor 108 is provided in an upper-side rear portion of the base body 100. An image photographed with a visible light camera 301 or an X-ray image generated by the image processor 75 is displayed on the image displaying monitor 108. Particularly, a base end portion of the image displaying monitor 108 is attached to the leading end portion of an arm 108a that is connected to the base body 100 so as to be turnable in a lateral direction (in a horizontal plane, in this embodiment). Therefore, the image displaying monitor 108 is laterally turnable about the center of the base end portion of the arm 108a. The image display of the image displaying monitor 108 is controlled by a display controller 710 to be described later.

A controller 71, a storage 73, and an image processor 75 are provided in the base body 100. The configurations and functions of the controller 71, storage 73, and image processor 75 are described later.

<Support Configuration of Support 30 and Accommodation Part 60>

As described above, the turning support base 150 is movably supported by the XYZ-direction moving mechanism 110. The turning support base 150 includes a base plate 152, a rear support 154, and a bearing support 156.

The base plate 152 is a plate-like member that is supported in a horizontal attitude at a position above the XYZ-direction moving mechanism 110.

The rear support 154 is formed into the plate shape as a whole. The rear support 154 may be formed of one plate-like member, or a plurality of plate-like members. FIG. 4 illustrates a configuration of the rear support 154 in which a plate-like member is attached on a rear surface side of another plate-like member having a hole at the center thereof so that the plate-like member closes the hole, and FIG. 3 schematically illustrates the rear support 154 as simplified one plate-like member.

The rear support 154 is fixed to the rear portion of the base plate 152 in an upright attitude with respect to the turning axis AX1. The rear support 154 may be fixed to the base plate 152 with an additional bracket and the like interposed therebetween, or directly be fixed to the base plate 152.

The bearing support 156 is fixed to the base plate 152 at a constant position attitude at a position where the bearing support 156 is separated on the side of the support 30 (that is, the front side) along the turning axis AX1 with respect to the rear support 154. The bearing support 156 is formed into the cyclic shape surrounding the turning axis AX1. The bearing support 156 may directly be fixed to the base plate 152 or rear support 154, or fixed to the base plate 152 or rear support 154 with an additional bracket and the like interposed therebetween.

The first bearing 160 is supported in the inner circumferential portion of the bearing support 156. In the configuration of the first bearing 160, an outside cyclic member 161 and an inside cyclic member 162 are relatively rotatably coupled to each other with a rolling element such as a cylindrical body or a spherical body interposed therebetween. The outside cyclic member 161 is relatively unrotatably fixed to the inside of the bearing support 156, and the inside cyclic member 162 is relatively unrotatably fixed to the outer circumferential portion of the turning support shaft 50. At this point, the inside cyclic member 162 is fixed to the outer circumference of the end portion of the pipe shape part 54 in the turning support shaft 50.

The turning support shaft 50 is rotatably supported by the first bearing 160 at a position separated from the turning driver 180 along the turning axis AX1.

The second bearing 165 is provided at a position separated from the first bearing 160 on the side of the support 30 (that is, the front side) along the turning axis AX1. In the configuration of the second bearing 165, an outside cyclic member 166 and an inside cyclic member 167 are relatively rotatably coupled to each other with a rolling element such as a cylindrical body or a spherical body interposed therebetween. The outside cyclic member 166 is relatively unrotatably fixed to the turning support shaft 50. At this point, the outside cyclic member 166 is fixed to the front side of the first turning support shaft 52 in the turning support shaft 50. More specifically, the outside cyclic member 166 is fixed to the main surface on the front side of the disc part 53 while projected toward the inner circumference side. The inside cyclic member 167 is relatively unrotatably fixed to the accommodation part support 62. That is, the accommodation part support 62 supports the second bearing 165 to rotatably support the turning support shaft 50, and the accommodation part support 62 is used as an element of the turning support base 150 on this point.

The turning support shaft 50 is rotatably supported by the second bearing 165 at a position, which is separated from the turning driver 180 along the turning axis AX1 and separated from the first bearing 160.

Thus, the turning support shaft 50 is rotatably supported above the seating 102 by the first bearing 160 and second bearing 165 of the turning support base 150, whereby the turning support base 150 rotatably supports the support 30 in the cantilever state.

Thus, when the turning support shaft 50 is rotatably supported by the first bearing 160 and second bearing 165, a moment load generated by the turning support shaft 50 provided along the turning axis AX1 is prevented from directly acting on the turning driver 180. Therefore, a deviation of an actual rotation axis of the turning support shaft 50 can be prevented.

Various modes may be considered as a configuration in which the turning support shaft 50 is rotatably supported. For example, the bearing may be a slide bearing or a rolling bearing. For the rolling bearing, the bearing may be a ball bearing or a roller bearing. Preferably, a cross roller bearing, which is resistant to a load such as a radial load and an axial load in various directions, is used as the bearing. Therefore, the support 30 is rotatably supported with high accuracy.

The accommodation part support 62 of the accommodation part 60 reaches the rear support 154 through the turning support shaft 50 and turning driver 180, and is relatively unrotatably fixed to the rear support 154. Therefore, the accommodation part support 62 and the accommodation part 60 is fixedly supported by the base body (support holder) 100, whereby the accommodation part 60 is unrotatably supported in the cavity 39. In the structure, the light emitter 67 is fixed to the base body (support holder) 100.

In the turning support base 150, an angle detector 170 and a drive switch 175 are provided around the turning support shaft 50.

The angle detector 170 is configured to detect the angle from a certain reference angle around the turning axis AX1 with respect to the base body (support holder) 100 of the support 30. Particularly, the angle detector 170 is configured to be capable of detecting the angle which is the center direction from the reference angle around the turning axis AX1 of the support 30. More particularly, the angle detector 170 includes a rotation detecting shaft 172, and a detector 173 such as an encoder. The rotation detecting shaft 172 is coupled to the turning support shaft 50 with a rotation transmission mechanism 171, such as a gear, interposed therebetween, and is rotatable in synchronization with the turning support shaft 50. The detector 173 detects a rotation angle of the rotation detecting shaft 172. The angle detector 170 can detect the angle in both the electric drive and the manual drive. The angle of the support 30 is described in detail later together with the description of the X-direction, the Y-direction, and the Z-direction.

The drive switch 175 is coupled to the turning support shaft 50 through a rotation transmission mechanism 176 such as a gear, and includes a braking shaft 177 that is rotatable in synchronization with the turning support shaft 50 and a brake 178 that can regulate the rotation of the braking shaft 177 and is fixed to the base plate 152. For example, a transmission member 50a fixed to the turning support shaft 50 and a transmission member 176a fixed to the braking shaft 177 come into contact with each other or mesh with each other so that the brake 178 can brake the braking shaft 177. Examples of the transmission members 50a and 176a include a roller or a gear. For example, an electromagnetic brake can be used as the brake 178. When the brake 178 is released, the support 30 is put into the manually rotating state.

In the case where the angle detector 170 detects the rotation angle from the reference angle of the support 30 to determine that the support 30 is rotated by more than or equal to a predetermined amount, the rotation of the braking shaft 177 is stopped by the drive switch 175, and therefore the rotation of the support 30 is stopped. Therefore, for example, the excess rotation of the support 30 can be prevented in the case where the user manually rotates the support 30.

<Rotation Drive Configuration of Support 30>

As illustrated in FIGS. 3 and 4, the support 30 and the turning support shaft 50 are driven and rotated by the turning driver 180 formed of a hollow motor 182. The turning driver 180 is an example of a turning mechanism.

The hollow motor 182 includes a hollow body 184 and a hollow rotation shaft 186. The hollow body 184 is formed into a cyclic shape. The hollow rotation shaft 186 is formed into a cyclic shape, and rotatably supported in the hollow body 184. One of an armature and a field element is incorporated in the hollow body 184, and the other is incorporated in the hollow rotation shaft 186. The hollow rotation shaft 186 is driven and rotated with respect to the hollow body 184 by action of both the armature and the field element. The hollow motor 182 is also configured as a motor that can control the rotation angle of a servo motor and the like, and the rotation angle (a rotation direction and a rotation amount) is controlled under the control of a processing control unit.

The hollow body 184 of the hollow motor 182 is fixed to the turning support base 150. At this point, a cyclic end surface on the rear side of the hollow body 184 is screwed on the rear support 154, whereby the hollow body 184 is fixed to the base plate 152. The hollow body 184 may be fixed to the base plate 152 with an additional bracket and the like interposed therebetween. More preferably, a direct drive type hollow motor can be used as the hollow motor.

The hollow rotation shaft 186 projects toward one side (front side) of the hollow body 184, and the rear end portion of the turning support shaft 50 is relatively unrotatably coupled to the end surface of the hollow rotation shaft 186 using a screw.

The hollow rotation shaft 186 is rotated by the drive of the turning driver 180, whereby the turning support shaft 50 and the support 30 are integrally driven and rotated while the rotation directions and rotation amounts of the turning support shaft 50 and support 30 are controlled.

<XYZ-Direction Moving Mechanism 110>

The XYZ-direction moving mechanism 110 in FIG. 5 includes a Y-direction moving mechanism 120 and a ZX-direction moving mechanism 130. The XYZ-direction moving mechanism 110 is controlled in each moving direction by a processing control unit.

In the description with reference to the Z-direction, the Z-direction is identical to the axial direction of the turning axis AX1, and is set to the horizontal direction in the example of FIG. 5. Both the X-direction and the Y-direction are orthogonal to the Z-direction, the Y-direction is set to the vertical direction in the example of FIG. 5, and the X-direction is set along the horizontal direction.

The Y-direction moving mechanism 120 is configured to be capable of elevating the turning support base 150 along the Y-direction, and the ZX-direction moving mechanism 130 is configured to be capable of moving the turning support base 150 in the Z-direction and X-direction together with the Y-direction moving mechanism 120.

More specifically, the ZX-direction moving mechanism 130 is provided on the seating 102.

The ZX-direction moving mechanism 130 includes a Z-direction moving mechanism 132 and an X-direction moving mechanism 142. The Z-direction moving mechanism 132 is provided on the seating 102, and the X-direction moving mechanism 142 is provided on the Z-direction moving mechanism 132.

The Z-direction moving mechanism 132 includes a pair of Z-direction guides 133, a Z-direction driver 134, and a Z-direction moving plate 135.

For example, the pair of Z-direction guides 133 is formed of a linear guide. The pair of Z-direction guides 133 is provided on the seating 102 in a parallel attitude along the Z-direction. The Z-direction moving plate 135 is supported by the pair of Z-direction guides 133 so as to be reciprocally movable in the Z-direction with respect to the seating 102.

The Z-direction driver 134 is formed of a linear driving mechanism including a motor and a ball screw, a linear motor, and a hydraulic cylinder, for example. The Z-direction driver 134 is provided between the seating 102 and the Z-direction moving plate 135, and configured to drive and move the Z-direction moving plate 135 in the Z-direction with respect to the seating 102.

For example, a guided member fixed to the Z-direction moving plate 135 is moved by the rotation of the ball screw of the Z-direction driver 134, which allows the Z-direction moving plate 135 to be driven and moved in the Z-direction.

The X-direction moving mechanism 142 includes a pair of X-direction guides 143, an X-direction driver 144, and an X-direction moving plate 145.

For example, the pair of X-direction guides 143 is formed of a linear guide. The pair of X-direction guides 143 is provided on the Z-direction moving plate 135 in the parallel attitude along the X-direction. The X-direction moving plate 145 is supported by the pair of X-direction guides 143 so as to be reciprocally movable in the X-direction with respect to the Z-direction moving plate 135.

The X-direction driver 144 is formed of a linear driving mechanism including a motor and a ball screw, a linear motor, and a hydraulic cylinder, for example. The X-direction driver 144 is provided between the Z-direction moving plate 135 and the X-direction moving plate 145, and configured to drive and move the X-direction moving plate 145 in the X-direction with respect to the Z-direction moving plate 135.

For example, a guided member fixed to the X-direction moving plate 145 is moved by the rotation of the ball screw of the X-direction driver 144, which allows the X-direction moving plate 145 to be driven and moved in the X-direction.

The Y-direction moving mechanism 120 provided on the X-direction moving plate 145 is maintained by the Z-direction moving mechanism 132 and the X-direction moving mechanism 142 so as to be capable of moving in the ZX-two-dimensional plane.

The Y-direction moving mechanism 120 includes a guide rod 121, a driving rod 125, an elevating guide 122, and an elevating driver 126.

The guide rod 121 and the driving rod 125 are long members that are provided while hanging down from the base plate 152.

The elevating guide 122 is provided on the X-direction moving plate 145, and the elevating guide 122 supports the guide rod 121 such that the guide rod 121 can be elevated. The elevating guide 122 is configured as a member having a vertically cylindrical space in which the guide rod 121 can be inserted, and the elevating guide 122 is vertically provided on the X-direction moving plate 145. A guide roller 122a (see FIG. 5) is rotatably supported in the elevating guide 122. When the guide rod 121 is inserted in the elevating guide 122, the guide roller 122a is pressed against the outer circumferential surface of the guide rod 121. The guide rod 121 can be elevated in the elevating guide 122 while the guide roller 122a is driven to rotate.

The elevating driver 126 drives the driving rod 125 up and down to drive the turning support base 150 including the base plate 152 up and down.

The elevating driver 126 includes a motor 126a and a transmission mechanism 126b that converts rotational motion of the motor 126a into linear motion. Various configurations such as a mechanism in which a rack gear and a pinion gear are combined and a ball screw mechanism can be used as the transmission mechanism 126b. Additionally, a configuration with a hydraulic cylinder can be used as the elevating driver.

The driving rod 125 is driven up and down by the elevating driver 126 while the guide rod 121 is elevatably guided by the elevating guide 122, thereby driving up and down the turning support base 150, the support 30, and the accommodation part 60.

The combination of the X-direction moving mechanism, Y-direction moving mechanism, and Z-direction moving mechanism of the XYZ-direction moving mechanism is not limited to the above example, but any moving mechanism is provided on the seating side or the turning support base side. One or two of the moving mechanisms in the XYZ-direction may be eliminated, or all the moving mechanisms in the XYZ-direction may be eliminated.

A XY-direction two-dimensional moving mechanism formed of the X-direction moving mechanism 142 and Y-direction moving mechanism 120 is used as an XY-table XY1 (not illustrated). Using the XY-table XY1, the turning center (the turning center for the X-ray photographing) of the X-ray generator 40 and X-ray detector 45 can be set to a place different from the mechanical turning axis during the X-ray photography.

When the turning support shaft 50 is rotated about the axis thereof, the X-ray generator 40 and the X-ray detector 45 turn with the axial center of the turning support shaft 50 as the turning center. Therefore, the turning support shaft 50 can be considered to be the mechanical turning axes of the X-ray generator 40 and X-ray detector 45.

In the first preferred embodiment, the axial center of the turning support shaft 50 is aligned with the axial center of the turning axis AX1. On the other hand, for example, in the CT photography, when the X-ray generator 40, the X-ray detector 45, and a photographing area FOV1 (not illustrated) are looked down from the Z-direction, the center of the photographing area FOV1 is set to a line connecting the center of the X-ray generator 40 and X-ray detector 45. Using the XY-table XY1, the axial center of the turning support shaft 50 is set to a place different from the center of the photographing area FOV1 on the line connecting the center of the X-ray generator 40 and X-ray detector 45. The turning center of the X-ray generator 40 and X-ray detector 45 during the X-ray photography can be set to the center of the photographing area FOV1 by the following control under the above geometrical condition. Hereinafter, the turning center during the X-ray photography is referred to as a virtual turning axis VX. Specifically, while the support 30 is turned about the axial center of the turning support shaft 50, the XY-table XY1 turns the turning support shaft 50 about the center of the photographing area FOV1 by the angle equal to the turning angle of the support 30 in synchronization with the turning. This enables the CT photography in which the photographing area FOV1 is irradiated with the X-ray cone beam BX1 while the X-ray generator 40 and the X-ray detector 45 turn with the center of the photographing area FOV1 as the turning center, namely, about the virtual turning axis VX. More preferably, the turning centers of the X-ray generator 40 and X-ray detector 45 are fixed turning centers.

Japanese Patent Application Laid-Open No. 2007-29168, which was filed by the inventor, discloses the configuration enabling the X-ray photography, and is incorporated by reference herein. The configuration disclosed in Japanese Patent Application Laid-Open No. 2007-29168, namely, the CT photography in a normal scan mode can be performed by turning the support 30 about the virtual turning axis VX. As used herein, the CT photography in the normal scan mode means the CT photography that is performed such that the whole range of the photographing area FOV1 is always irradiated with the X-ray cone beam BX1 while at least one of the X-ray generator 40 and the X-ray detector 45 is not offset with respect to the photographing area FOV1 when viewed from the Z-direction.

The configuration disclosed in International Publication No. 2009/063974, namely, the CT photography in an offset scan mode is incorporated by reference herein. The CT photography in the offset scan mode can be performed in an area wider than that of the CT photography in the normal scan mode. It is assumed that the CT photography is performed on a CT photography area FOV2 (not illustrated) wider than the photographing area FOV1 in the offset scan mode.

In the CT photography in the offset scan mode, at least one of the X-ray generator 40 and the X-ray detector 45 is offset with respect to the photographing area FOV2 when viewed from the Z-direction, resultantly the whole range of the photographing area FOV2 is irradiated with the X-ray while the photographing area FOV2 is partially irradiated with the X-ray cone beam BX1, and the projection data of at least 180 degrees is obtained with respect to the whole range of the photographing area FOV2.

Geometrically, the virtual turning axis VX is also offset from the center of the photographing area FOV2 by the offset of at least one of the X-ray generator 40 and the X-ray detector 45, the support 30 is turned about the center axis of the turning support shaft 50, and the turning support shaft 50 is rotated by the XY-table XY1 such that the virtual turning axis VX is turned by the angle equal to the turning angle of the support 30 in synchronization with the turning of the support 30 with the center of the photographing area FOV2 as the turning center while the virtual turning axis VX becomes the instantaneous turning center of the X-ray generator 40 and X-ray detector 45.

Resultantly, the X-ray generator 40 and the X-ray detector 45 turn with the center of the photographing area FOV2 as the turning center during the X-ray photography. The turning center during the X-ray photography can also be considered to be a new virtual turning axis.

The angle of the support 30 will be described below referring to FIG. 1. In the following description, it is assumed that the turning axis AX1 is the Z-axis extending in the Z-direction, and that Z1 is a specific point on the Z-axis. It is assumed that a plane XY1 is a plane that spreads in a two-dimensional direction defined by the X-direction and Y-direction around the point Z1, that a reference point SP1 is specific one point on the plane XY1 that is not positioned at the point Z1 on the plane XY1, and that a reference line SL1 is a straight line extending from the point Z1 through the point SP1. A point XP1 different from the reference point SP1 is defined on the plane XY1, and it is assumed that a line XL1 is a straight line extending from the point Z1 through the point XP1. When viewed from an axial direction of the Z-axis, an angle θr formed between the reference line SL1 and the line XL1 is an angle formed between the line XL1 and the reference line SL1.

At this point, in order to discuss a numerical value of the angle, it is considered that clockwise movement is started around the point Z1 of the point XP1 from the point XP1 on the reference line SL1.

Assuming that a 0 o'clock direction is a direction from the point Z1 toward the point XP1 located at a moving start point, the angle formed between the line XL1 and the reference line SL1 (=θr) is 0 degree when the point XP1 at the moving start point is located on the reference line SL1. The 0 o'clock direction, namely, the angle of the 0 degree can be considered to be a reference angle.

When the point XL1 moves to a 3 o'clock direction, an angle formed between the line XL1 and the reference line SL1, namely, the reference angle is 90 degrees. Similarly, the angle is 180 degrees when the point XL1 reaches a 6 o'clock direction, the angle is 270 degrees when the point XL1 reaches a 9 o'clock direction, and the angle is 360 degrees when the point XL1 reaches a 12 o'clock direction.

The facts are applied to the angle of the support 30, and the angle formed between the support 30 and the reference line SL1 can be considered to be the angle of the support 30. In this case, assuming that a specific point XP1 is set on the support 30 for the purpose of calculation while a straight line XL1 passing through the specific point XP1 from the turning axis AX1 is set for the purpose of calculation, and the angle between the straight line XL1 and the reference line SL1 can be considered to be the angle of the support 30. The specific point XP1 is set to any place. For example, it is conceivable that the point XP1 is set to an X-ray beam focal point located in an anode of the X-ray tube of the X-ray generator 40. In this case, the straight line XL1 is a line connecting the turning axis AX1 and above described X-ray beam focal point located in the anode of the X-ray tube, and the straight line XL1 rotates when the support 30 rotates.

<Controller 71>

Figure 6:
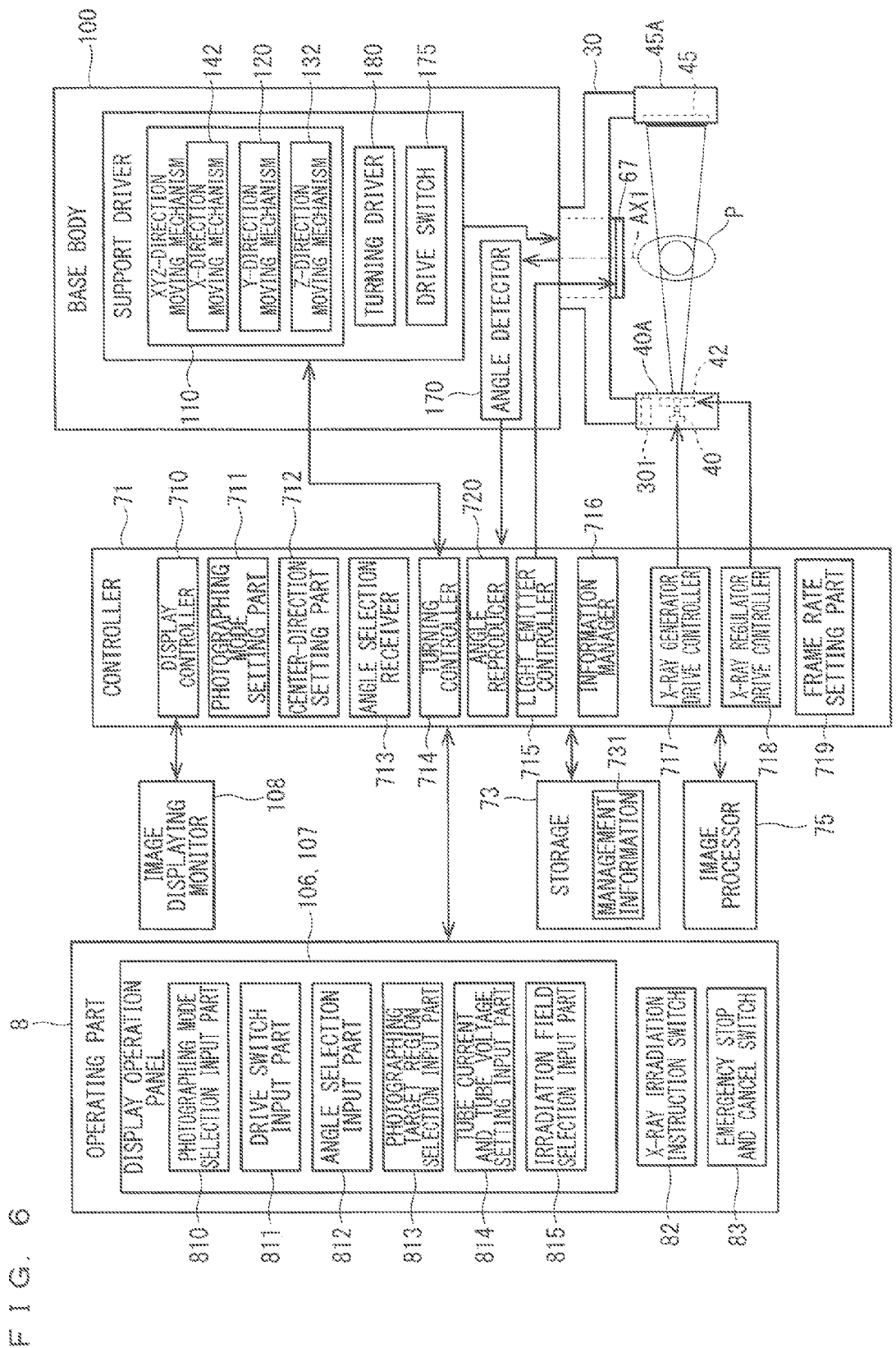
FIG. 6 is a block diagram illustrating a connection relationship between a controller and other elements in the first preferred embodiment.

FIG. 6 is a block diagram illustrating a connection relationship between the controller 71 and other elements in the first preferred embodiment. The controller 71 includes a general computer including a CPU, a ROM, and a RAM. The controller 71 is configured to control the operation (of the turning arm driver of the base body 100) of the medical X-ray photographing apparatus 20 based on the input from the operator through an operating part 8 including display operation panels 106 and 107, an X-ray irradiation instruction switch 82, and an emergency stop and cancel switch 83.

A display controller 710, a photographing mode setting part 711, a center-direction setting part 712, an angle selection receiver 713, a turning controller 714, a light emitter controller 715, an information manager 716, an X-ray generator drive controller 717, an X-ray regulator drive controller 718, a frame rate setting part 719, and an angle reproducer 720 in FIG. 6 are functional modules, which are constructed such that a CPU of the controller 71 operates according to a program. Some of or all the functional modules may be constructed by a dedicated circuit in a hardware manner.

The display controller 710 is configured to control the image display of the image displaying monitor 108. Various X-ray images generated by image processing of the image processor 75 are displayed on the image displaying monitor 108 in addition to the image photographed with the visible light camera 301.

The photographing mode setting part 711 is configured to switch the photographing mode of the X-ray photography performed by the turning controller 714 among a CT photographing mode, a tomosynthesis photographing mode, a panoramic photographing mode, and a simple X-ray photographing mode. The panoramic photographing mode is one that is performed in order to acquire one image of the whole mouth (or a part of the mouth) along a tooth row. The simple X-ray photographing mode is one in which the subject P is photographed with the support 30 fixed at a predetermined angle. The tomosynthesis photography and the CT photography will be described with reference to FIGS. 7 and 8.

Figure 7:
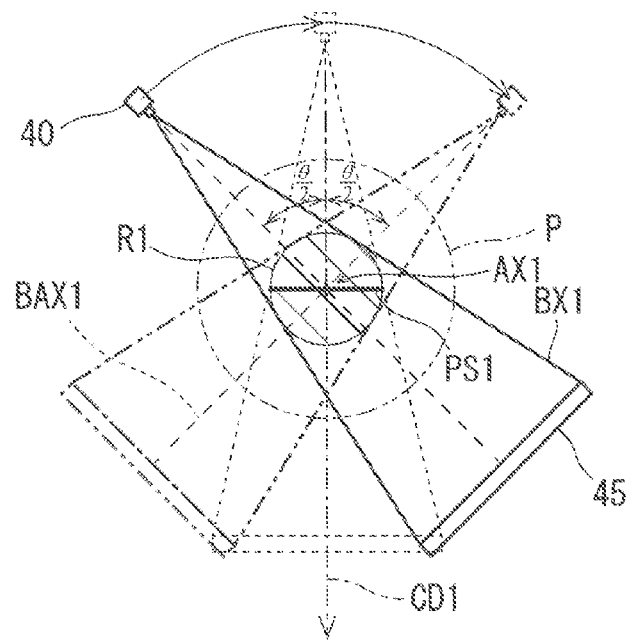
FIG. 7 is a conceptual view illustrating tomosynthesis photography.
Figure 8:
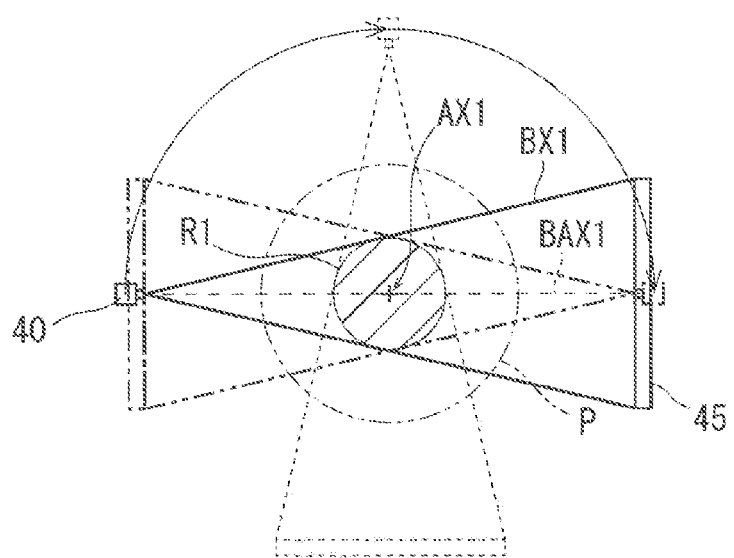
FIG. 8 is a conceptual view illustrating CT photography.

FIG. 7 is a conceptual view illustrating the tomosynthesis photography. FIG. 8 is a conceptual view illustrating the CT photography. FIGS. 7 and 8 illustrate moving loci of the X-ray generator 40 and X-ray detector 45 when the X-ray generator 40 and the X-ray detector 45 are viewed along the turning axis AX1.

In the tomosynthesis photography, as illustrated in FIG. 7, an observation target region of the subject P is irradiated with the X-ray cone beam BX1. The subject P is irradiated with the X-ray cone beam BX1 while the X-ray generator 40 and the X-ray detector 45 are turned such that a swing angle θ of the center axis (X-ray axis BAX1) of the X-ray cone beam BX1 about the turning axis AX1 becomes greater than or equal to 30 degrees and less than 180 degrees, thereby collecting the X-ray projection image at a predetermined frame rate.

On the other hand, in the CT photography, as illustrated in FIG. 8, the subject P is irradiated with the X-ray cone beam BX1 while the X-ray generator 40 and the X-ray detector 45 are turned such that the swing angle of the X-ray axis BAX1 of the X-ray cone beam BX1 is greater than or equal to 180 degrees (more preferably, greater than or equal to 360 degrees), thereby collecting the X-ray projection image at a predetermined frame rate.

In the CT photography, for a cylindrical photographing area R1 that is always irradiated with the X-ray cone beam BX1, the image having a comparable three-dimensional information amount can be reconstructed even if any visual line direction (a direction in which a three-dimensional target object is viewed) is set. On the other hand, in the tomosynthesis photography, the image (tomosynthesis image) having a sufficient three-dimensional information amount is obtained with respect to a sectional plane PS1 in which a center direction CD1 (the orientation of the X-ray axis BAX1 when the X-ray generator 40 is rotated by a half angle (θ/2) of the swing angle θ) passing through the center of the swing angle θ is set to the visual line direction. However, because the three-dimensional information about the photographing area R1 runs short as the visual line direction separates from the center direction CD1, the sufficient tomosynthesis image is difficult to reconstruct.

In the tomosynthesis photography, compared with the CT photography, because of the small swing angle of the support 30, advantageously an exposure dose of the subject is small, and the photographing time is short. For example, in the case where the visual line direction set to the image diagnosis target region of the patient is fixed to a certain degree before, during, or after a surgery, the tomosynthesis photography is suitably performed.

Returning to FIG. 6, the center-direction setting part 712 sets the center direction CD1 (see FIG. 7) passing through the center of the swing angle of the support 30 in the X-ray tomosynthesis photography in which the X-ray generator 40 emits the X-ray toward the X-ray detector 45. In the medical X-ray photographing apparatus 20, the operator manually rotates the support 30 to dispose the support 30 at the angle at which the axial direction of the X-ray axis BAX1 becomes the center direction, and the angle detector 170 reads an operating angle when the operating part 8 performs predetermined operation. The center-direction setting part 712 is configured to set the center direction based on the angle range corresponding to the read operating angle. The center direction may be fixed before the operating angle is fixed, or the swing angle may be selected from previously-set some angle ranges while only the center direction is fixed. As described above, the center direction is the direction corresponding to the visual line direction in which the most preferable tomosynthesis image is obtained. When the operator manually rotates the support 30 to set the center direction, the operator can intuitively align the center direction with the desired visual line direction. Therefore, the tomosynthesis image suitable for the image diagnosis can be produced. The center direction can arbitrarily be set from a predetermined reference angle, but the center direction is not necessarily located immediately above as illustrated in FIG. 7. Alternatively, an oblique angle may be set to the center direction.

The center-direction setting part 712 is configured to receive a command to assign the center direction while the image photographed with the visible light camera 301 is displayed on the image displaying monitor 108 or the display operation panels 106 and 107. Therefore, because the operator can set the center direction while confirming the image, the center direction can easily be set to the desirable visual line direction.

In setting the center direction CD1, the subject P is irradiated with the visible beams emitted from the positioning visible beam emitters 681 and 682. Therefore, because a relative positional relationship between the support 30 and the subject P can correctly be understood, the center direction CD1 can properly be set. In setting the center direction CD1, the positioning light irradiation part 34a also emits the visible light. Therefore, the position can be specified where the subject P is irradiated with the X-ray. Accordingly, the center direction CD1 can properly be set.

The center-direction setting part 712 can set the center direction based on the angle input through the operating part 8. For example, it is conceivable that the assignment of the angle of the X-ray generator 40 (or X-ray detector 45) is received, and that the axial direction of the X-ray axis BAX1 passing through the angle is set to the center direction.

The angle selection receiver 713 is configured to receive a command to select the swing angle of the support 30 turning in the X-ray photography from a plurality of predetermined angles. Based on the turning angle received by the angle selection receiver 713, the turning controller 714 controls the turning driver 180 to turn the support 30. For example, in the tomo synthesis photography, a plurality of angles (for example, 60 and 90 degrees) are previously provided in a range where the swing angle is greater than or equal to 30 degrees and less than 180 degrees. In the CT photography, a plurality of angles of 180 degrees or more (for example, 180 and 360 degrees) are previously provided. Using the angle selection receiver 713, the swing angle is selected from the plurality of previously-prepared angles, so that the swing angle can easily be set.

Here, the angle selection receiver 713 and the turning controller 714 work as a swing-angle setting part.

The swing angle can arbitrarily be set. For example, the operator may directly input the swing angle through the operating part 8 for assignment. Alternatively, the operator manually rotates the support 30 by the angle corresponding to the desired swing angle, and the angle detector 170 may read the turning angle of manual rotation to set the swing angle. In this case the angle detector 170 and the turning controller 714 work as a swing-angle setting part.

The turning controller 714 controls the turning of the support 30 by controlling support drivers including the turning driver 180. For example, in the tomosynthesis photography, the turning controller 714 controls the turning driver 180 such that the support 30 is turned about the center direction set by the center-direction setting part 712 at an necessary swing angle (or input swing angle) received by the angle selection receiver 713.

The light emitter controller 715 controls the light emitter 67 according to the turning condition of the support 30. In the tomosynthesis photography, examples of the turning condition include the swing angle of the support 30 received by the angle selection receiver 713 and the orientation of the center direction set by the center-direction setting part 712. That is, the light emitter controller 715 lights on, turns off, or blinks the light emitting elements 671 and 672 of the light emitter 67 to display the set swing angle and orientation of the center direction.

An example of the mode in which a swing angle θ and the center direction CD1 are displayed by the light emitter 67 will be described with reference to FIGS. 9 and 10.

Figure 9:
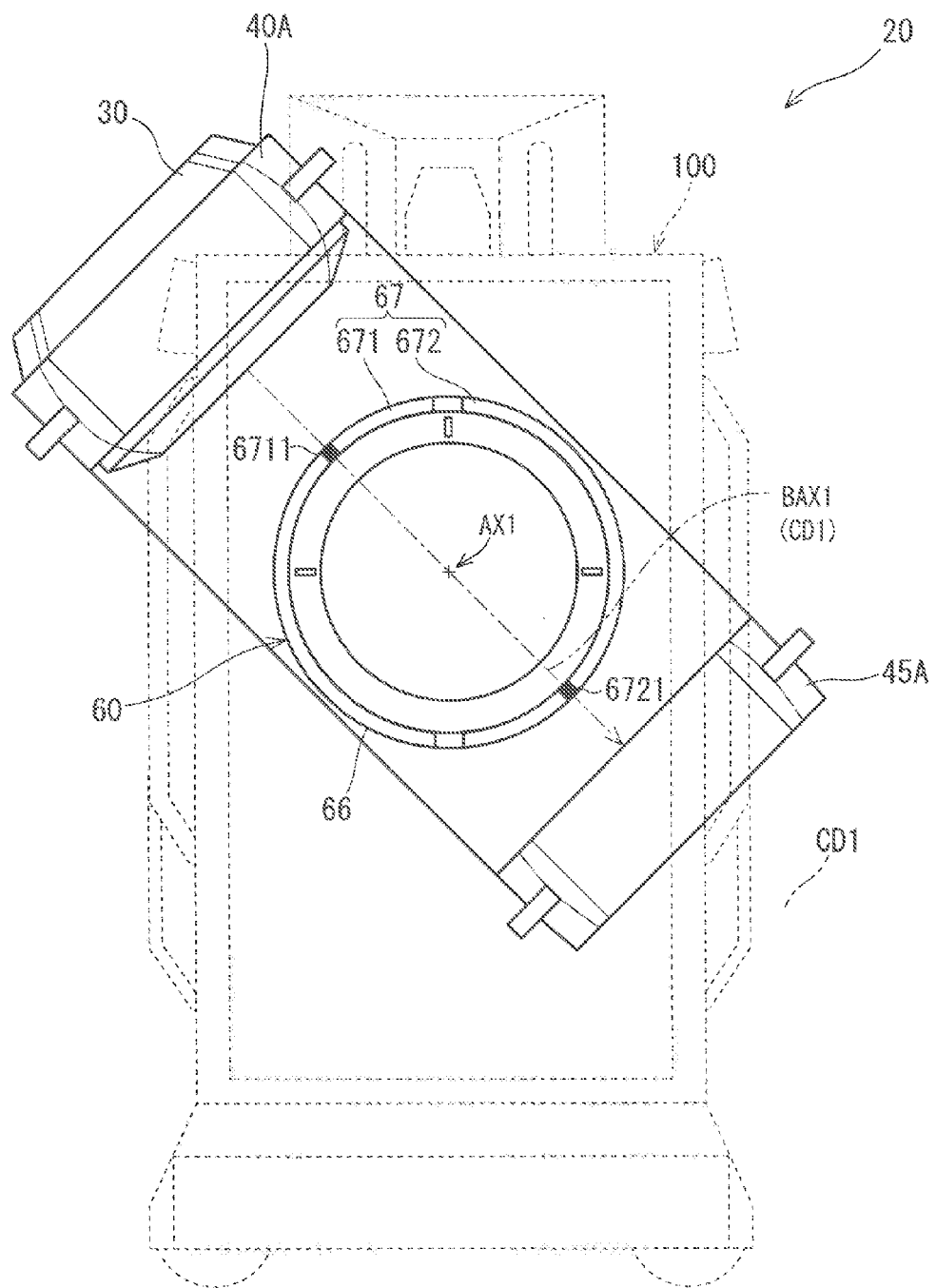
FIG. 9 is a schematic front view illustrating a support and a light emitter of the first preferred embodiment.
Figure 10:
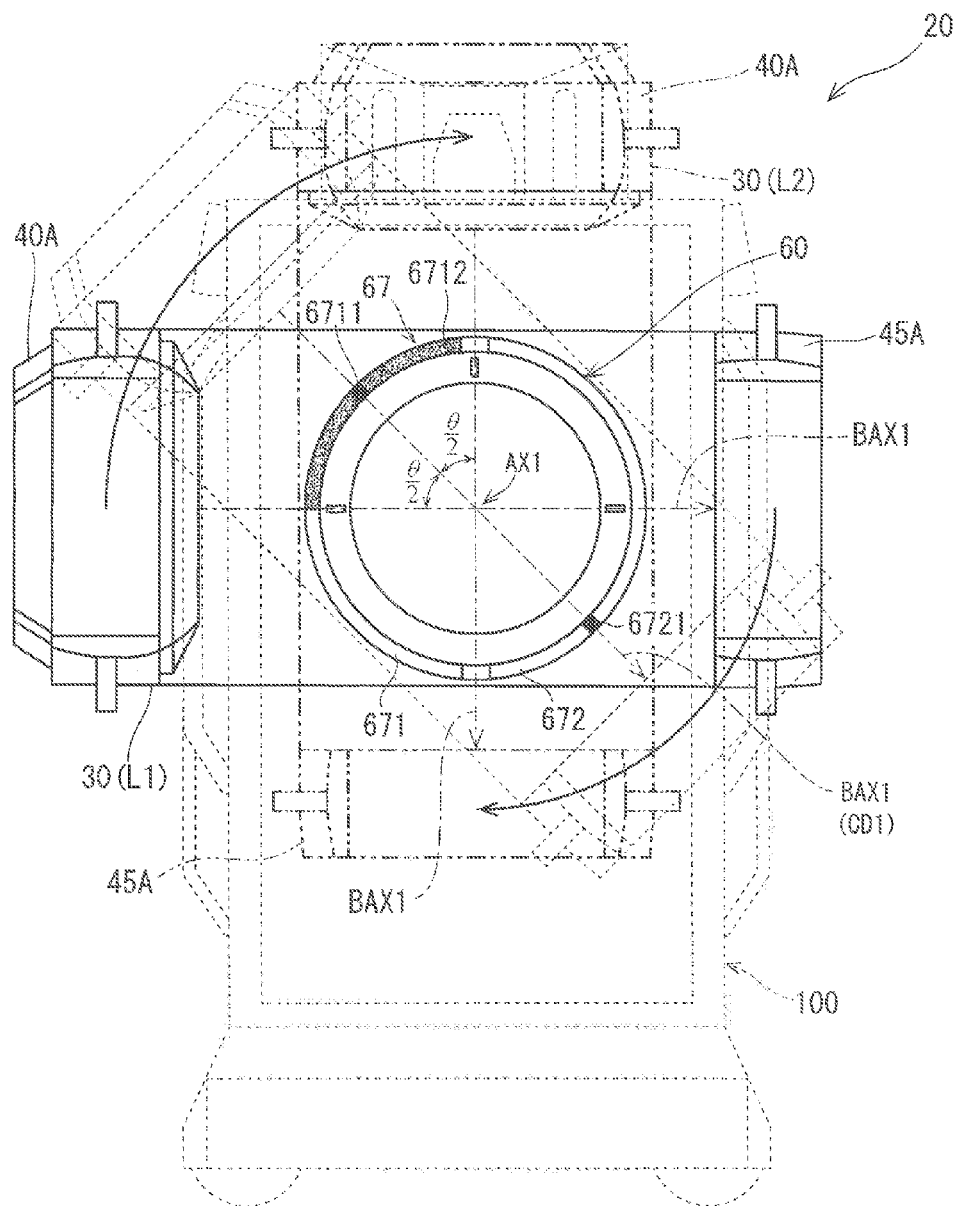
FIG. 10 is a schematic front view illustrating the support and the light emitter of the first preferred embodiment.

FIGS. 9 and 10 are schematic front views illustrating the support 30 and the light emitter 67 of the first preferred embodiment. FIG. 9 illustrates the light emission state of the light emitter 67 at a time point the center direction CD1 is set. FIG. 10 illustrates the light emission state of the light emitter 67 at a time point the center direction CD1 and the swing angle θ are set.

As illustrated in FIG. 9, when the center direction CD1 for the tomosynthesis photography is set, the light emitter controller 715 performs the control such that portions 6711 and 6721 facing each other along the X-ray axis BAX1 parallel to the center direction CD1 emit the light in the light emitting elements 671 and 672 formed of the plurality of LEDs. Therefore, the light emitter controller 715 performs the light emission display so as to indicate the center direction CD1. As used herein, the term "light emission display" means the display in which a light emission mode (including lighting, turn-off, and blinking) of a target portion varies from that of other portions to distinguish the target portion from other portions. The operator can recognize the center direction CD1 set for the tomosynthesis photography by virtually connecting the portions 6711 and 6712 using a straight line. The orientation (that is, the orientation from the X-ray generator 40 toward the X-ray detector 45) of the center direction CD1 can be recognized by changing the light emission mode between the portions 6711 and 6712 such that the portions 6711 and 6712 emit the light in different colors.

When the swing angle θ is set, the light emitter controller 715 causes the portion 6712 of the angle range corresponding to the swing angle θ in the light emitting elements 671 and 672 to emit the light as illustrated in FIG. 10. In the example of FIG. 10, the portion 6712 is an arc portion corresponding to the turning range of the X-ray axis BAX1 in the light emitter 67 disposed on the circle having the center of the turning axis AX1. Thus, the light emission display of the turning range enables the operator to visually recognize the magnitude and turning range (in this case, the turning range of the X-ray generator 40) of the swing angle θ of the support 30 during the X-ray photography.

In a case where operation to change the center direction is herein performed, the light emission display of the light emitting element is also changed in accordance with the change of the center direction. If the swing angle is determined, the change of the center direction is followed by the change of the position of the swing angle, and thus the position of the light emission display of the light emitting element indicating the range of the swing angle is also changed.

In a case where the swing angle is changed to another swing angle, the range of the light emission display is changed in accordance with the change of the swing angle.

In the tomosynthesis photography, as illustrated in FIG. 10, the turning controller 714 turns the support 30, which is stopped at a first angle L1 (L1 as start angle) deviated from the center direction CD1 by a half angle (θ/2) of the swing angle θ, to a second angle L2 (L2 as end angle) deviated by an opposite half angle (θ/2) with respect to the center direction CD1.

The light emitter controller 715 controls the light emission of the light emitter 67 according to other operating situations of the medical X-ray photographing apparatus 20. Examples of the operating situations include the state where the photographing condition is fixed to complete turning preparation of the support 30, the state where the turning preparation is not completed (turning preparation state), the on and off state of the electromagnetic brake (brake 178) switching between the manual drive and the electric drive of the support 30 (the on and off state of the electromagnetic lock), the state where the emergency stop and cancel switch 83 is operated to stop the operation of the medical X-ray photographing apparatus (emergency stop state), the state where the X-ray is currently emitted (X-ray irradiation state), the turning direction of the support 30 set for the photographing, the X-ray irradiation direction, and the turning angle and the turning direction of the support 30. The unique light emission display may be performed in each of the operating situations.

The angle reproducer 720 calls the angle indicating the center direction stored in the storage 73 using a calling operating part (not illustrated), and reproduces the angle. The angle reproducer and the calling operating part may perform the calling and reproduction of the swing angle in addition to the calling and reproduction of the angle indicating the center direction. Not only the center angle but also the swing angle may be stored in the storage.

The angle reproducer 720 can store in the storage 73 the center angle temporarily set by the center-direction setting part 712, and reproduce the angle such that the turning arm is driven to have the set angle based on the operation of the calling operating part (not illustrated).

Returning to FIG. 6, the information manager 716 stores, in the storage 73 as management information 731, center direction CD1 set to the individual subject by the center-direction setting part 712 and the swing angle θ in association with each other, and reads the management information 731 from the storage 73 based on a read command. Thus, the center direction CD1 and the swing angle θ are read later, so that the photographing condition for the tomo synthesis photography can easily be understood after the tomo synthesis photography.

The angle reproducer 720 may constitute a part of the information manager 716, and the angle reproducer 720 and the information manager 716 may separately be provided so as to share the information about the storage 73.

In addition to the center direction CD1 and the swing angle θ, the information manager 716 stores, in the storage 73 as the management information 731, a tube current and a tube voltage provided to the X-ray tube of the X-ray generator 40, and patient information in association with one another. Accordingly, the tomosynthesis photography performed on each patient can easily be reproduced by reading the management information 731.

The light emitter controller 715 refers to the read management information 731 to perform the light emission display of the center direction CD1 and swing angle θ using the light emitter 67. Therefore, in the tomosynthesis photography to be reproduced, whether the center direction CD1 and the swing angle θ are proper can be checked in advance.

The X-ray generator drive controller 717 is configured to control the X-ray generator 40. Specifically, the X-ray generator drive controller 717 controls the tube current and tube voltage that are supplied to the X-ray generator 40. Therefore, the on and off of the X-ray emitted from the X-ray generator 40, the X-ray intensity, and the like can be controlled.

The X-ray regulator drive controller 718 controls the X-ray regulator 42. Specifically, the X-ray regulator drive controller 718 drives the movement of the shielding plates 421 and 422 (and the horizontal shielding plates) of the X-ray regulator 42, which makes the X-ray beam in the shape (various X-ray cone beams) corresponding to the X-ray photographing mode.

The frame rate setting part 719 is configured to set a frame rate when the X-ray detector 45 outputs the electric signal in the CT photography or the tomosynthesis photography. In the case where the frame rate is densely set, because three-dimensional information having high spatial resolution is obtained, so that the accuracy of the reconstruction can be enhanced. However, a photographing time is lengthened in the case where the turning of the support 30 needs to be performed at a relatively slow speed.

The frame rate setting part 719 may be configured to set the frame rate to a constant value in the period in which the support 30 turns by the swing angle θ, or to set the frame rate to a variable value. For example, in the tomosynthesis photography of FIG. 7, the frame rate setting part 719 relatively densely sets the frame rate in the turning range of the support 30 where the X-ray axis BAX1 falls within a predetermined angle from the center direction CD1, and relatively coarsely sets the frame rate in other turning ranges. Therefore, the resolution of the tomosynthesis image that is reconstructed with the center direction CD1 as the visual line direction can be improved while the photographing time is shortened.

Depending on the frame rate set by the frame rate setting part 719, the light emitter controller 715 may change the light emission state of the light emitter 67. For example, the coloring, brightness, and density of the colored portion of the light emitter 67 may be changed between the high and low frame rates. In the case where the frame rate is set to the variable value, the color, the brightness, and the light emission density (an area for the light emitter portion per unit area) may be changed between the dense and coarse frame rates.

The light emitter 67 may perform the light emission display of the turning range of the support 30 in the CT photography.

For example, as described above, the X-ray cone beam BX1, namely, the support 30 turns 180 degrees or more, or preferably 360 degrees or more, to perform the CT photography, and, in the case of the turning of 180 degrees, the light emission display of the turning range is performed, and, in the case of the turning of 360 degrees, the light emission display of the turning range, namely, the whole range is performed.

The image processor 75 is the processing control unit formed of, for example, a general microcomputer including a CPU, a ROM, and a RAM. The image processor 75 performs calculation processing of processing the X-ray projection image based on the electric signal obtained with the X-ray detector 45 by the X-ray photography and generating various X-ray images such as a CT image, a tomosynthesis image, and a panoramic image. The generated X-ray image is displayed on the image displaying monitor 108. There are various X-ray image display modes according to the diagnostic purpose. For example, in displaying the tomosynthesis image on the image displaying monitor 108, an image photographed with the visible light camera 301 may be overlapped on a part of the tomosynthesis image from the direction corresponding to the visual line direction that is set to generate the tomosynthesis image. Therefore, the position of the tomosynthesis image corresponding to the diagnosis target region of the subject P can easily be specified.

The X-ray image generated by the image processor 75 may be displayed on the display operation panels 106 and 107 in addition to the image displaying monitor 108, displayed on another display through a wired or wireless communication line, or recorded in a recording medium such as a magnetic recording medium, an optical recording medium, and a flash memory.

<Operating Part 8>

The display operation panels 106 and 107 constituting the operating part 8 includes a photographing mode selection input part 810, a drive switch input part 811, an angle selection input part 812, a photographing target region selection input part 813, a tube current and tube voltage setting input part 814, and an irradiation field selection input part 815.

Figure 11:
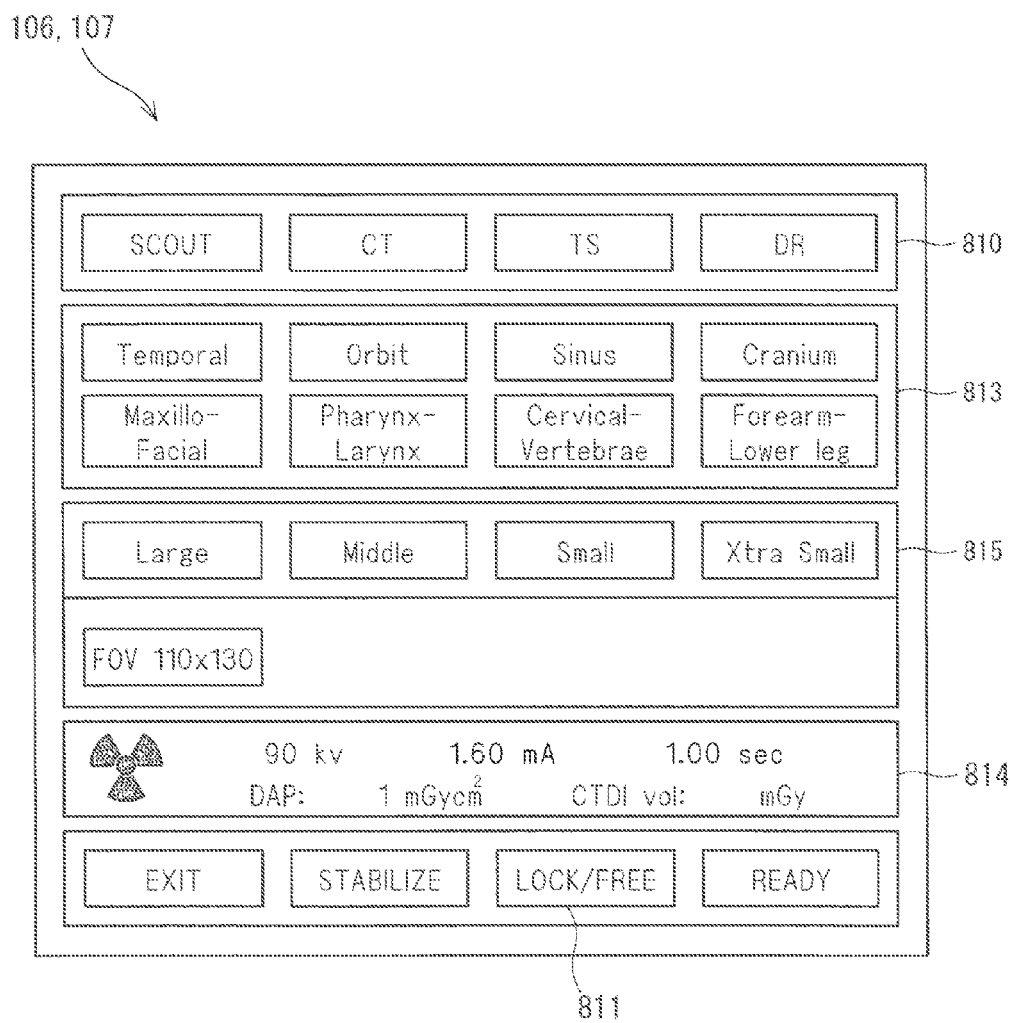
FIG. 11 is a view illustrating an example of a screen displayed on a display operation panel of the first preferred embodiment.

FIG. 11 is a view illustrating an example of a screen displayed on the display operation panel 106 or 107 of the first preferred embodiment. As illustrated in FIG. 11, in the display operation panel 106 or 107, the input part includes a plurality of buttons, and each button is pressed for selection. Therefore, input information allocated to each button is transmitted to the controller 71.

The photographing mode selection input part 810 is the input part for selecting the photographing mode from the scout photography, the CT photography, the tomo synthesis photography, and the simple photography. The photographing mode setting part 711 sets the photographing mode selected through the photographing mode selection input part 81 to the photographing mode of the X-ray photography performed by the turning controller 714. The photographing mode may be switched between at least one of the simple X-ray photographing mode and CT photographing mode and the tomo synthesis photographing mode.

The drive switch input part 811 is the input part that performs the switching operation of the turning of the support 30 between an electric-powered mode in which the turning controller 714 performs the electric control of the support 30 and a manual mode in which the support 30 can manually be rotated. When the manual mode is set by operating the drive switch input part 811, the drive switch 175 releases the electromagnetic brake of the brake 178. Therefore, the support 30 is put into the manually rotatable state. Thus, the turning drive mode of the support 30 is switched between the electric-powered mode and the manual mode by performing the on and off operation of the electromagnetic brake.

In the electric-powered mode, the electromagnetic brake may be configured to be basically on, and be off only while the support 30 is driven and turned, and the turning drive mode may be configured to be switched to the manual mode when the drive switch input part 811 performs the off operation of the electromagnetic brake, and be switched to the electric-powered mode when the drive switch input part 811 performs the on operation of the electromagnetic brake.

The drive switching may be performed simply based on whether to excite the hollow motor 182. When the drive switch input part 811 is operated to set the manual mode, excitation of the hollow motor 182 is released. The release of excitation disables a force to brake the turning of the turning support shaft 50, namely, the turning of the support 30, making it easy to manually turn the support 30. The release of excitation and the release of the electromagnetic brake of the brake 178 are configured to be performed together. When the drive switch input part 811 is operated to set the electric-powered mode, excitation of the hollow motor 182 occurs. The occurrence of excitation makes it difficult or impossible to manually turn the support 30. It is preferred that braking by the electromagnetic brake of the brake 178 be performed while the drive of the support 30 is stopped and be released while the support 30 is driven and turned.

As for transmission of a rotational force from the hollow motor 182 to the support 30, a mechanical element that switches between enabling and disabling of transmission of the rotational force may be disposed at any position between the hollow motor 182 and the support 30.

For example, a clutch (not illustrated) may be disposed at a position around the turning axis AX1 between hollow motor 182 and the support 30. Examples of the position include a position between the rear end of the turning support shaft 50 and the hollow rotation shaft 186 and a position between the hollow motor 182 and the hollow rotation shaft 186.

The angle selection input part 812 is the input part that is operated when the operator selects the desired swing angle θ from the plurality of predetermined angles. The angle selection receiver 713 sets the angle selected through the angle selection input part 812 to the swing angle θ of the X-ray axis BAX1.

The photographing target region selection input part 813 is the input part that is operated when the photographing target region is selected in performing the X-ray photography. An option of the photographing condition suitable for each photographing target region is previously stored in the storage 73, and the option of the photographing condition corresponding to the photographing target region selected through the photographing target region selection input part 813 is called. As used herein, the term "the option of the photographing condition" means for example, the plurality of angles that are displayed by the angle selection input part 812 for selection, and the magnitude of each of the plurality of irradiation fields that are displayed by the irradiation field selection input part 815 for selection. That is, the option of the photographing condition corresponding to the selected photographing target region is displayed on the display operation panels 106 and 107. The display operation may be displayed on the image displaying monitor 108.

The tube current and tube voltage setting input part 814 is operated when the X-ray generator drive controller 717 sets the tube current and tube voltage that are supplied to the X-ray tube of the X-ray generator 40. The irradiation field selection input part 815 is operated in selecting the magnitude of the irradiation field. The X-ray regulator drive controller 718 drives the X-ray regulator 42 such that the spread of the X-ray cone beam BX1 is matched with the irradiation magnitude selected by the irradiation field selection input part 815.

Figure 12:
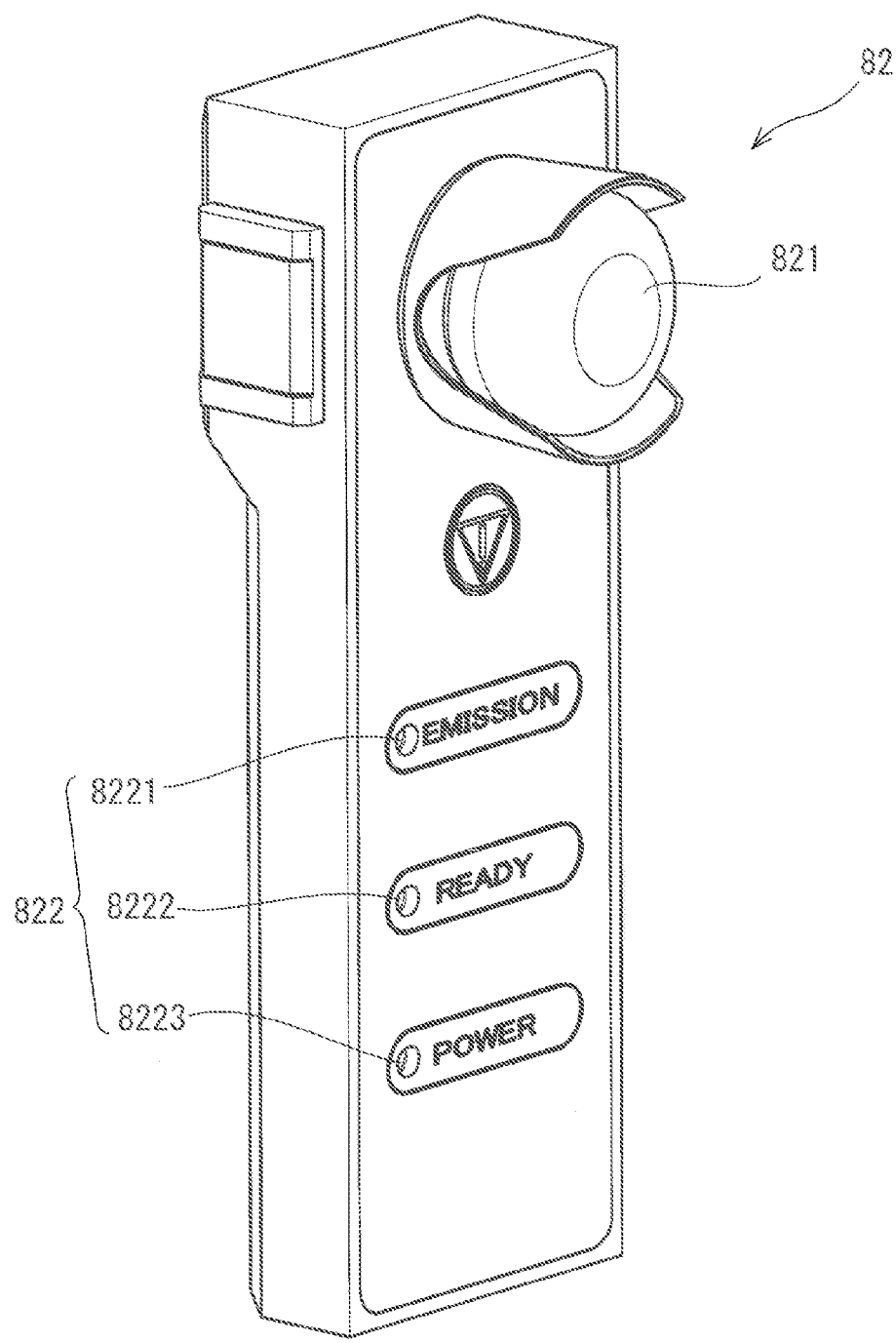
FIG. 12 is a perspective view illustrating an X-ray irradiation instruction switch of the first preferred embodiment.

FIG. 12 is a perspective view illustrating the X-ray irradiation instruction switch 82 of the first preferred embodiment. The X-ray irradiation instruction switch 82 includes a switch 821 that is pressed by the operator at the beginning of the X-ray irradiation and an LED display 822. The LED display 822 includes an emission LED 8221, a readiness LED 8222, and a main power LED 8223. The emission LED 8221 is lit while the X-ray generator 40 emits the X-ray. The readiness LED 8222 is lit when the support 30 moves to the photographing starting angle to complete the preparation of the X-ray photography. The main power LED 8223 is lit when a main power switch of the medical X-ray photographing apparatus 20 is in the on state. In the tomosynthesis photography and the CT photography, the turning of the support 30 and the X-ray irradiation are simultaneously performed by operating the X-ray irradiation instruction switch 82. The X-ray irradiation instruction switch 82 is formed of a dead man switch. When the operator separates a finger from the X-ray irradiation instruction switch 82, the turning of the support 30 is stopped and the X-ray irradiation is stopped.

The emergency stop and cancel switch 83 in FIG. 1 is operated to stop the operation of the medical X-ray photographing apparatus 20, namely, the turning of the support 30 and the X-ray irradiation, or to cancel the stop of the turning of the support 30 and the X-ray irradiation to perform the operation again. As illustrated in FIGS. 1 and 2, the emergency stop and cancel switch 83 is provided immediately below the display operation panels 106 and 107. Therefore, the operator can quickly operate the emergency stop and cancel switch 83 when operating the display operation panel 106 and 107 during the X-ray photography.

When the operation of the medical X-ray photographing apparatus 20 is stopped by the emergency stop and cancel switch 83, the light emitter controller 715 may cause the whole or part of the light emitter 76 to emit the light. For example, the light emitter 76 may emit the light in a unique color indicating the emergency stop state or the stop cancel state.

<Description of Operation>

Figure 13:
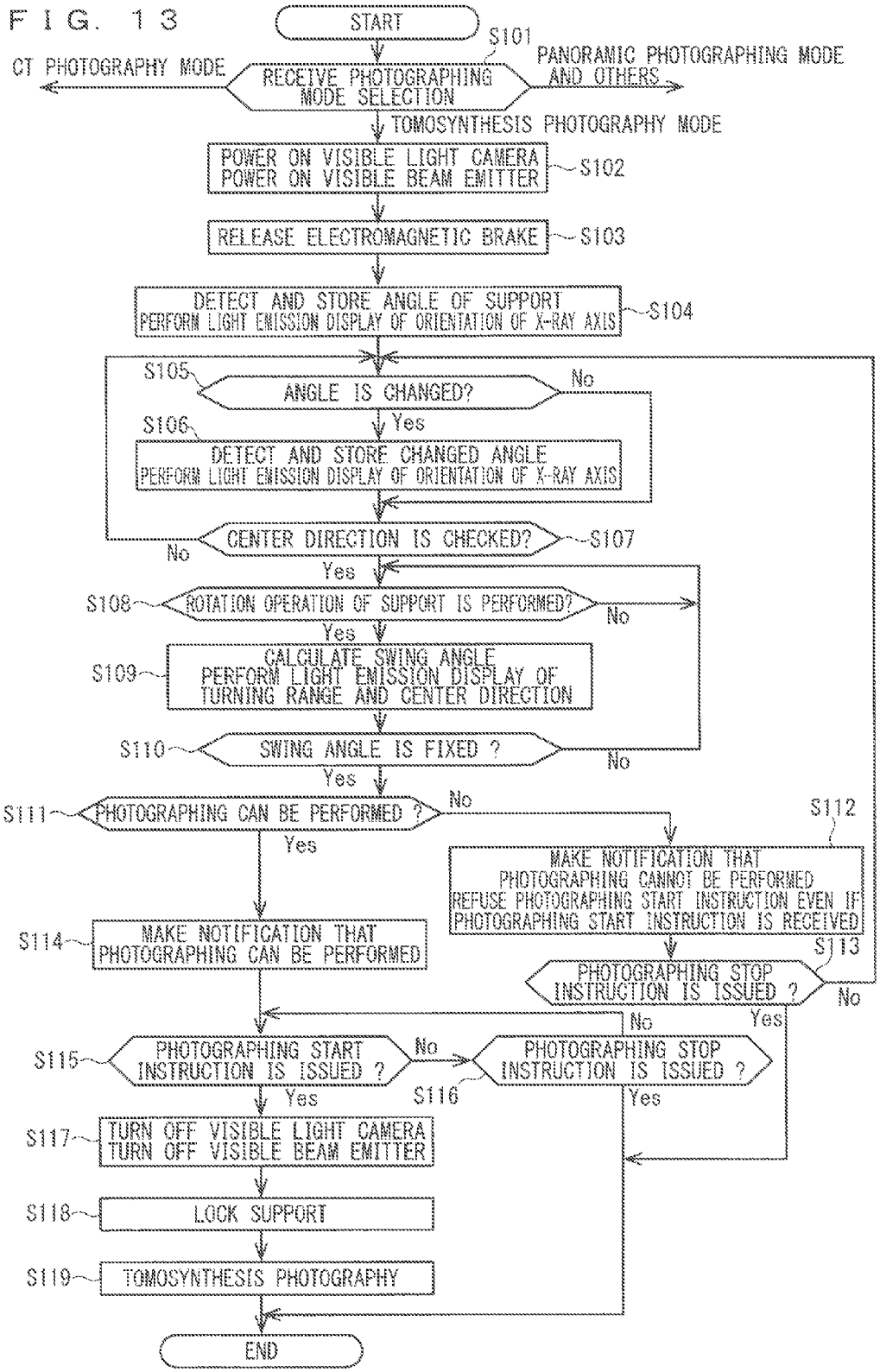
FIG. 13 is a view illustrating an operational flow of the medical X-ray photographing apparatus of the first preferred embodiment.
Figure 14:
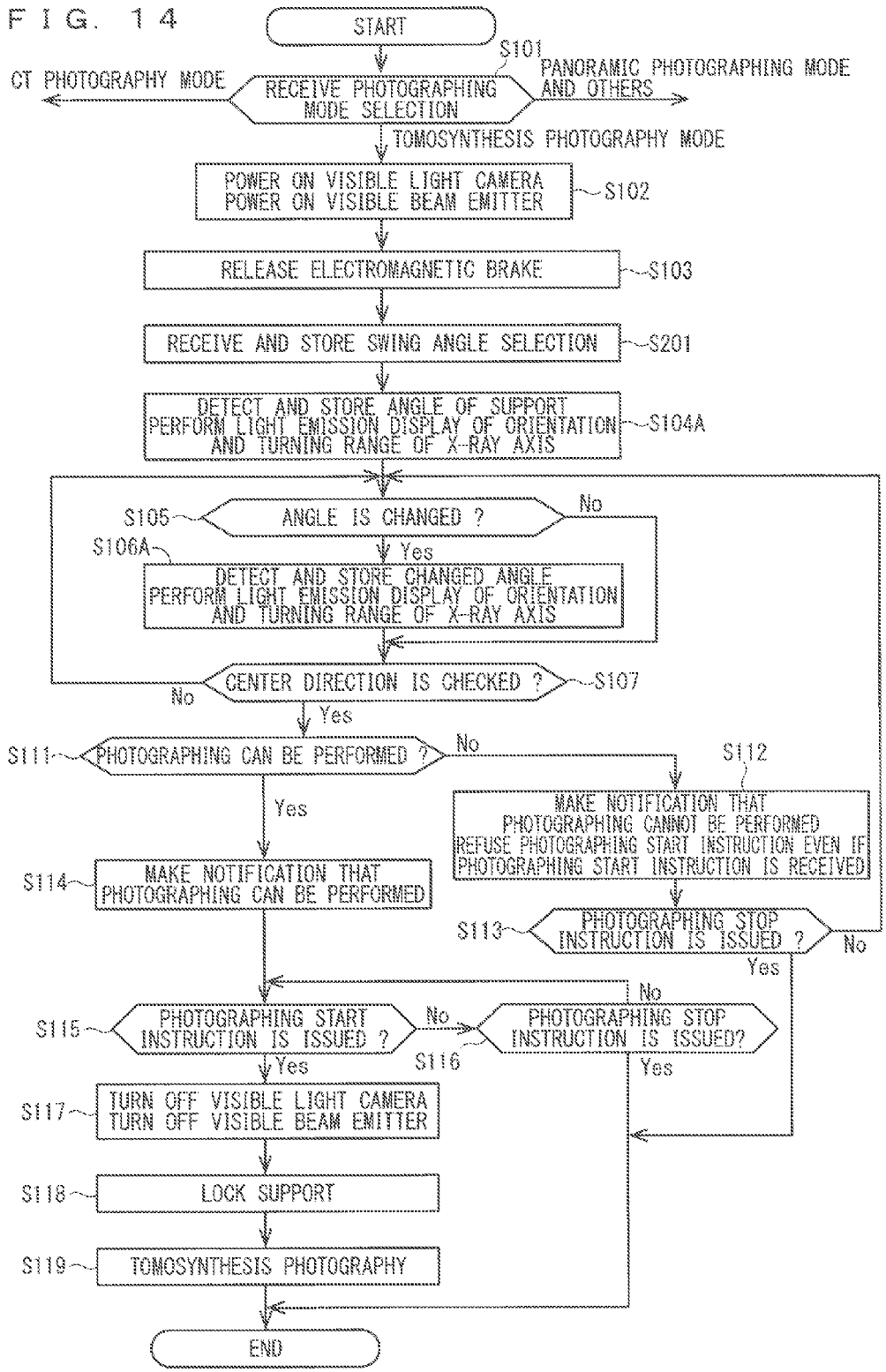
FIG. 14 is a view illustrating an operational flow of the medical X-ray photographing apparatus of the first preferred embodiment.

The operation of the medical X-ray photographing apparatus 20 will be described below. FIGS. 13 and 14 are views illustrating an operational flow of the medical X-ray photographing apparatus 20 of the first preferred embodiment. Although FIGS. 13 and 14 illustrate a flow of the tomosynthesis photography, FIGS. 13 and 14 differ from each other in the setting mode of the swing angle θ. Specifically, FIG. 14 illustrates the mode in which the swing angle θ is set through the operating part 8 (angle selection input part 812), and FIG. 13 illustrates the mode in which the support 30 is manually rotated to set the swing angle θ. Each mode will be described below.

<Setting of Swing Angle θ by Turning Support 30>

As illustrated in FIG. 13, the selection of the photographing mode is received through the photographing mode selection input part 810 (Step S101). At this point, it is assumed that the tomosynthesis photographing mode is selected.

Then, the visible light camera 301 and the visible beam emitters 681 and 682 are powered on (Step S102). The visible light camera 301 is enabled to perform the photographing, and the subject P can be positioned using the visible beam.

The drive switch input part 811 is operated to release the electromagnetic brake of the brake 178 (Step S103). Therefore, the support 30 can manually be rotated. The electromagnetic brake may automatically be released at a time point the tomosynthesis photographing mode is selected in Step S101.

Then, the angle detector 170 detects the angle of the support 30. The light emitter 67 performs the light emission display of the orientation of the X-ray axis BAX1 of the support 30 disposed at the angle, namely, the center direction (Step S104).

Then, as illustrated in FIG. 9, the operator manually rotates the support 30 to match the orientation of the X-ray axis BAX1 with the desirable visual line direction with respect to the subject P. Therefore, the controller 71 determines whether the angle of the support 30 is changed (Step S105). When the angle of the support 30 is changed, the post-rotation-operation angle of the support 30 is appropriately read by the angle detector 170, and temporarily stored in the RAM or the storage 73. The light emitter 67 performs the light emission display of the post-rotation-operation orientation of the X-ray axis BAX1 (Step S106, see FIG. 9).

Then, the controller 71 determines whether the center direction CD1 is decided (Step S107). For example, the determination in Step S107 is made based on whether a predetermined operation input is performed in order to decide the center direction CD1. When the center direction CD1 is not decided, the controller 71 performs the pieces of processing in Steps S105 to S107 again. When the center direction CD1 is decided, the controller 71 goes to Step S108 to set the swing angle θ.

In the flowchart of FIG. 13, the swing angle θ is set by rotating the support 30. In Step S108, the angle detector 170 determines whether the support 30 is rotated. The processing in Step S108 is repeatedly performed until the rotation operation is detected.

As illustrated in FIG. 10, when the operator rotates the support 30 up to the irradiation starting position where the X-ray irradiation is started, the rotation angle α of the support 30 from the center direction CD1 to the irradiation starting position is detected by the angle detector 170. Because the center direction CD1 passes through the center of the swing angle θ, a double angle 2α in which the rotation angle α is doubled becomes the swing angle θ. Thus, the swing angle θ is calculated. As illustrated in FIG. 10, the light emitting elements 671 and 672 of the light emitter 67 emit the light in the portion corresponding to the turning range of the support 30, thereby performing the light emission display of the turning range and the center direction CD1 (Step S109).

When the operator performs the operation to rotate the support 30 in order to set the swing angle θ between Steps S107 and S108, the light emitter 67 performs the light emission display of the orientation of the X-ray axis BAX1 indicating the center direction CD1 detected in Step S104. Preferably, while the turning range is changed and adjusted in the rotation operation, the turning range of the support 30 is calculated in real time according to the turning amount, and the light emission display of the turning range is performed. Therefore, the operator can easily understand how much the support 30 is rotated from the center direction CD1. Accordingly, the swing angle θ can be set to the preferable angle.

If the orientation of the X-ray axis BAX1 indicating the above-mentioned center direction CD1 is CD1A, and the current angle between the direction CD1A and the support 30 formed by the operator performing the operation to rotate the support 30 is αA, the light emitter 67 performs the light emission display of the range of the angle αA in the lateral direction around the direction CD1A in real time. The light emission display of the range between the angle −αA and the direction CD1A and the light emission display of the range between the direction CD1A and the angle +αA may be performed in different manners.

Although the double angle 2α of the detected rotation angle α may be set to the swing angle θ without any changes, the rotation angle α is changed to a predetermined default angle, and the double angle of the default angle may be set to the swing angle θ. For example, a default angle β closest to the rotation angle α is selected from a plurality of predetermined default angles, and a double angle 2β of the default angle β may be set to the swing angle θ.

Then, the controller 71 determines whether the swing angle θ is decided (Step S110). For example, the determination in Step S110 is made based on whether the predetermined operation input is performed in order to decide the swing angle θ. When the swing angle θ is not decided, the controller 71 returns to Step S108 to detect the rotation operation of the support 30.

When the swing angle θ is decided in Step S110, the controller 71 determines whether the tomosynthesis photography can be performed. For example, whether the turning of the support interferes with an obstacle in the photographing during a surgery is checked.

When determining that the tomosynthesis photography cannot be performed in Step S110, the controller 71 notifies the user that the tomosynthesis photography cannot be performed through the display operation panels 106 and 107 or the image displaying monitor 108. Even if the photographing starting instruction is input from the X-ray irradiation instruction switch 82, the photographing starting instruction is refused (Step S112). The notification that the tomosynthesis photography cannot be performed may be made through the light emitter 67. For example, the light emitter controller 715 may light or turn off the light emitter 67 in a unique light emission mode indicating that the tomosynthesis photography cannot be performed.

Subsequent to step S112, the controller 71 determines whether a photographing stop instruction is issued (Step S113). When the photographing stop instruction is issued, the controller 71 stops the tomosynthesis photography. When the tomosynthesis photography is continued, the controller 71 returns to Step S105 to receive the setting of the center direction CD1 again.

When determining that the tomosynthesis photography can be performed in Step S110, the controller 71 notifies the user that the tomosynthesis photography can be performed through the display operation panels 106 and 107 or the image displaying monitor 108 (Step S114). The notification that the tomosynthesis photography can be performed may be made through the light emitter 67. For example, the light emitter controller 715 may light or turn off the light emitter 67 in a unique light emission mode indicating that the tomosynthesis photography can be performed.

Then, the controller 71 determines whether the photographing starting instruction is issued (Step S115). The determination in Step S115 is made based on the existence of the input from the X-ray irradiation instruction switch 82. When the photographing starting instruction is not issued, the controller 71 determines whether the photographing stop instruction is issued (Step S116). When the photographing stop instruction is issued, the controller 71 stops the tomosynthesis photography. When the photographing stop instruction is not issued, the controller 71 returns to Step S115.

When the photographing starting instruction for the tomosynthesis photography is issued in Step S115, the controller 71 stops the photographing of the visible light camera 301 and the visible beam emission from the visible beam emitters 681 and 682 (Step S117).

Then, the controller 71 actuates the electromagnetic brake of the brake 178 to lock the support 30 (Step S118). Therefore, the support 30 cannot manually be operated, but the support 30 is put into the electric drive state. The controller 71 performs the tomosynthesis photography (Step S119).

Thus, in the first preferred embodiment, the settings of the center direction CD1 and swing angle θ are performed by the rotation operation of the support 30. Therefore, tomosynthesis photography condition can intuitively be set.

<Setting of Swing Angle θ Through Operating Part 8>

The flowchart in FIG. 14 will be described below. The process in FIG. 14 similar to that in FIG. 13 is designated by the identical numeral, the description is omitted, and only a different point is described.

In Steps S108 to S110 of the flowchart in FIG. 13, the swing angle θ in the tomosynthesis photography is set by receiving the rotation operation of the support 30. On the other hand, in the flowchart of FIG. 14, after the electromagnetic brake is released in Step S103, the controller 71 receives the operation input to select swing angle θ through the angle selection input part 812 (Step S201). When the operator operates the angle selection input part 812 to select the angle, the angle selection receiver 713 sets the selected angle to the swing angle θ.

The angle detector 170 detects the angle of the support 30, and the light emitter 67 performs the light emission display of the orientation of the X-ray axis BAX1 (Step S104A). At this point, the light emitter controller 715 may set the orientation of the X-ray axis BAX1 to a tentative center direction CD1, and emit the light in the portion corresponding to the turning range of the swing angle θ about the tentative center direction CD1 in the light emitter 67.

When the rotation operation of the support 30 for the purpose of setting the center direction CD1 is detected in Step S105, the post-rotation-operation angle of the support 30 is appropriately read by the angle detector 170, and temporarily stored in the RAM or the storage 73. The light emitter 67 performs the light emission display of the post-rotation-operation orientation of the X-ray axis BAX1 of the support 30 (Step S106A). At this point, the light emitter controller 715 may set the orientation of the X-ray axis BAX1 to a tentative center direction CD1, and emit the light in the portion corresponding to the turning range of the swing angle θ about the tentative center direction CD1 in the light emitter 67.

The controller 71 may be configured to perform Step S201 after or in parallel to Steps S104A and S105. More specifically, the controller 71 may be configured to perform Step S201 after Step S106A. In these cases, "LIGHT EMISSION DISPLAY OF TURNING RANGE" in Step S104A is changed to be performed after Step S201.

Because the pieces of processing (Steps S107 to S119) subsequent to Step S106A are substantially similar to those subsequent to Step S106 in FIG. 13, the description is omitted.

In the case where the swing angle θ is set in the flowchart of FIG. 14, namely, the swing angle θ is set through the operating part 8, the swing angle θ can correctly be set. The swing angle θ is selected from the plurality of predetermined angles, so that the photographing condition of the tomosynthesis photography can quickly be set.

<2. Second Preferred Embodiment>

A second preferred embodiment will be described below. In the following description, the element having the function similar to that of the already-described element is designated by the identical numeral or the numeral to which an alphabet is added, and the detailed description is occasionally omitted.

Figure 15:
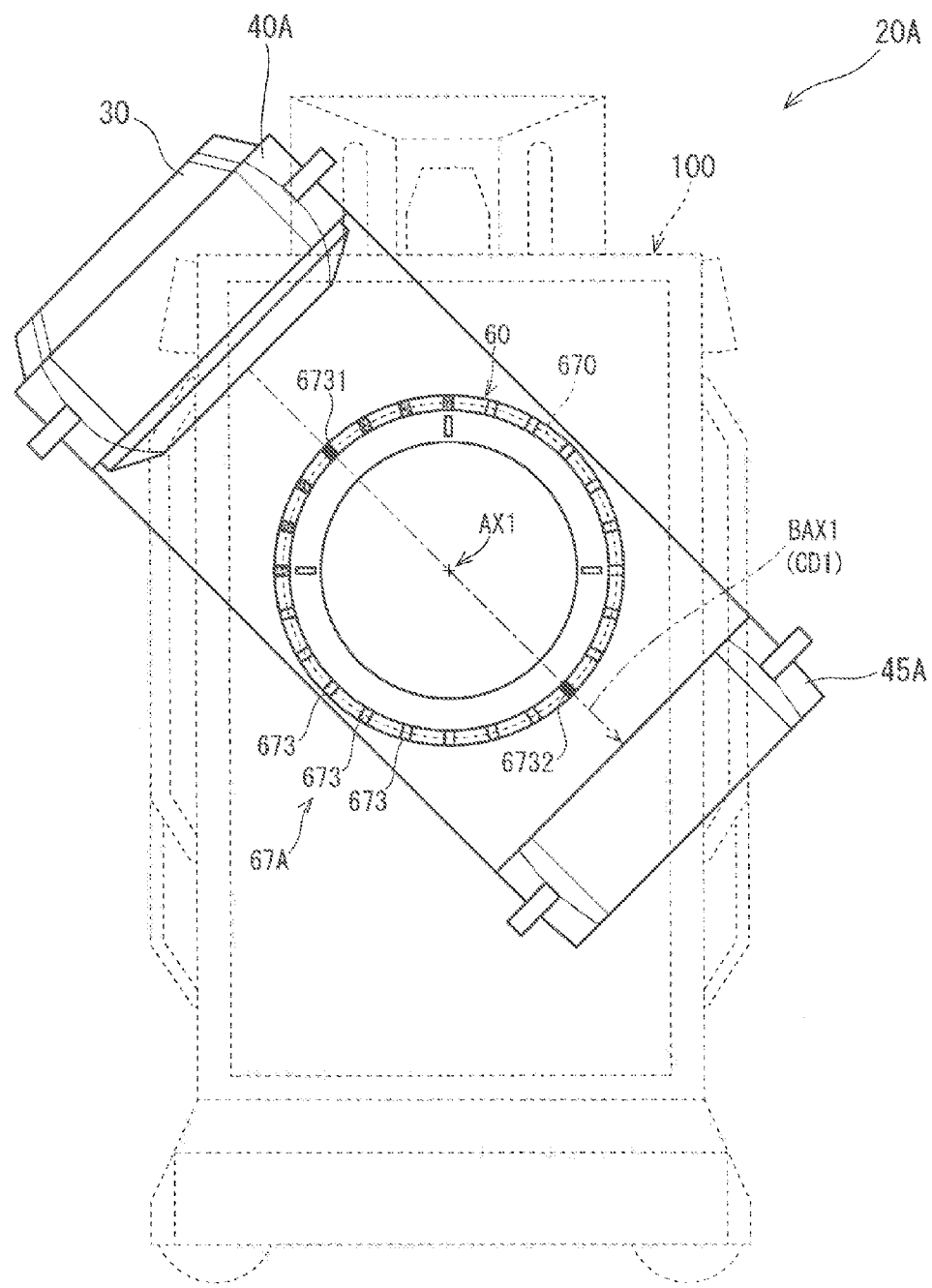
FIG. 15 is a schematic front view illustrating a medical X-ray photographing apparatus according to a second preferred embodiment.

FIG. 15 is a schematic front view illustrating a medical X-ray photographing apparatus 20A according to a second preferred embodiment. In the medical X-ray photographing apparatus 20A, a light emitter 67A includes a plurality of light emitting elements 673 disposed at constant intervals of angle along a perfect-circle virtual loop line 670 surrounding the turning axis AX1. Each light emitting element 673 includes at least one color LED. Alternatively, the light emitting element 673 may be formed of a monochrome LED or an electric bulb.

As illustrated in FIG. 15, in the plurality of light emitting elements of the light emitter 67A, a pair of light emitting elements 6731 and 6732 disposed in the facing state along the center direction CD1 emits light in the case where the light emission display of the center direction CD1 set for the tomosynthesis photography is performed. Therefore, the center direction CD1 set in the medical X-ray photographing apparatus 20A can easily be understood. In the case where the swing angle θ is set for the tomosynthesis photography, one or a plurality of light emitting elements 673, which are located in a half-angle range of the swing angle θ around the center direction CD1 in a lateral direction, may emit the light in all the light emitting elements 673 (except for the light emitting elements 6731 and 6732). Therefore, the turning range of the support 30 can easily be understood.

<3. Third Preferred Embodiment>

Figure 16:
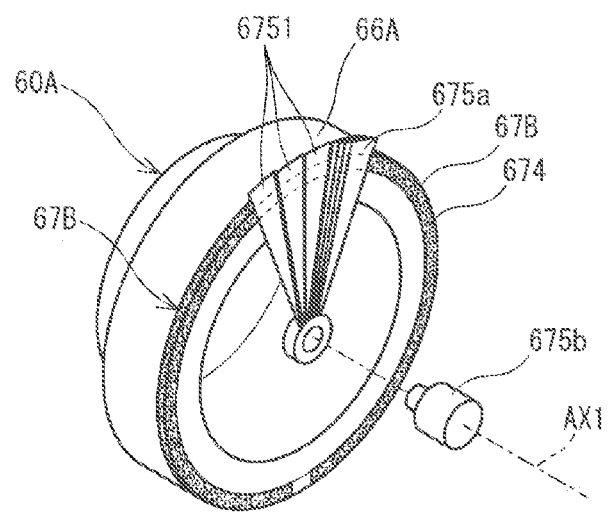
FIG. 16 is a schematic perspective view illustrating a light emitter according to a third preferred embodiment.

FIG. 16 is a schematic perspective view illustrating a light emitter 67B according to a third preferred embodiment. The light emitter 67B of the third preferred embodiment includes a light emitting element 674, a light shielding member 675a, and an actuator 675b.

The light emitting element 674 is provided at the end edge of the ring 66A in the accommodation part 60A attached to the cavity 39. The light emitting element 674 is not necessarily configured such that the light emission mode can be changed in each part unlike the light emitting element 671, but the light emitting element 674 may be configured such that the whole light emitting element 674 uniformly emits the light. For example, the light emitting element 674 may be formed of a fluorescent light or a neon tube in addition to the LED.

The light shielding member 675a is configured so as to be spread into a fan shape about the turning axis AX1 or closed by the actuator 675b. Specifically, the light shielding member 675a is formed of a plurality of substantially triangular plate-like members 6751 overlapped with each other in the axial direction. Each plate-like member 6751 extends in a radial direction perpendicular to the turning axis AX1, and is longer than a radius of the light emitting element 674. Therefore, in the case where the light emitter 67B is viewed along the turning axis AX1, each plate-like member 6751 is provided so as to shield the light emitted from the light emitting element 674. Although each plate-like member 6751 is movable in the circumferential direction, the plate-like members 6751 adjacent to each other in the axial direction are coupled to each other such that a gap is not generated when the plate-like members 6751 spread in the fan shape.

The light shielding member 675a is disposed in front of the light emitting element 674, which allows the shielding of the light emitted from the light emitting element 674. When viewed from the outside, the light emitter 67B can perform the light emission display such that light emission is generated only in the partial angle range around the turning axis AX1. In the case where the light emitter 67B is used, the light emission display of the turning range can be performed by light shielding control.

<4. Fourth Preferred Embodiment>

Figure 17:
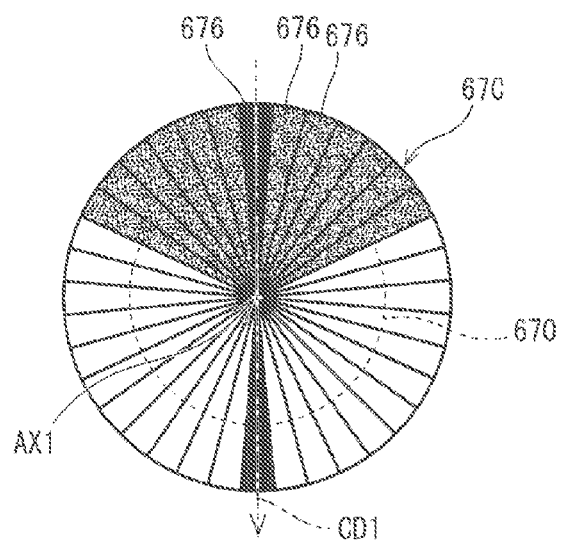
FIG. 17 is a schematic front view illustrating a light emitter according to a fourth preferred embodiment.

FIG. 17 is a schematic perspective view illustrating a light emitter 67C according to a fourth preferred embodiment. In the light emitter 67C, the light emission surface is formed of a plurality of fan-shape light emitting elements 676 arranged around the turning axis AX1 without a gap. Each light emitting element 676 is disposed on the cyclic virtual loop line 670 surrounding the turning axis AX1. That is, the light emitter 67C in planar shape is a mode of the light emitter disposed on the virtual loop line. The light emitter controller 715 is configured such that each light emitting element 674 is lit or turned off in an individual light emission mode.

In the case where the light emitter 67C is used, for example, the light emission display of the center direction CD1 can be performed by lighting or turning off the light emitting element 674 on the center direction CD1 set for the tomosynthesis photography. The light emission display of the turning range of the support 30 can be performed by lighting or turning off at least one light emitting element 674 in the turning range corresponding to the swing angle θ set for the tomosynthesis photography.

<5. Fifth Preferred Embodiment>

Figure 18:
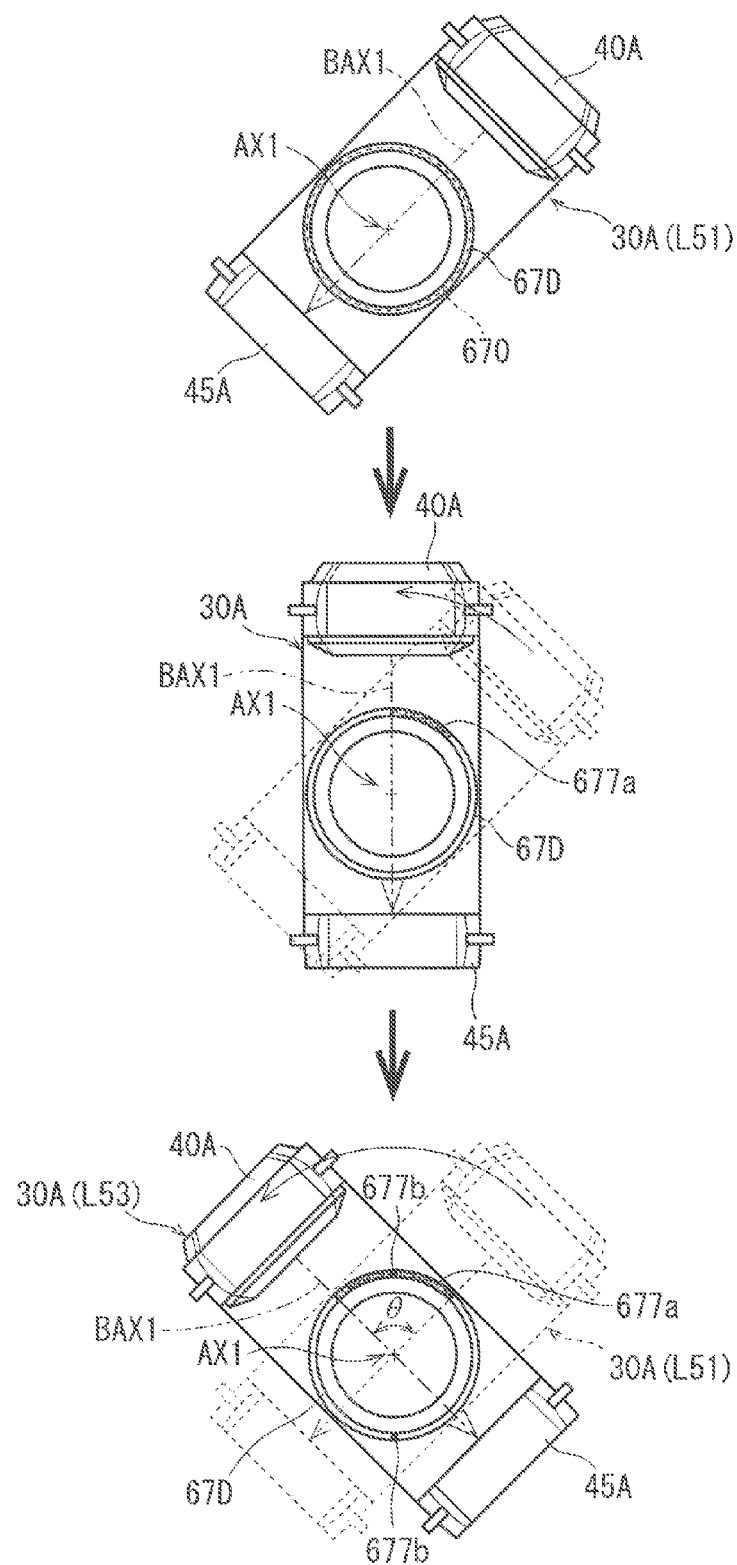
FIG. 18 is a schematic front view illustrating a support according to a fifth preferred embodiment.

FIG. 18 is a schematic front view illustrating a support 30A according to a fifth preferred embodiment. The ring 66 of the first preferred embodiment is separated from the support 30. Therefore, the light emitter 67 provided in the ring 66 does not rotate together with the support 30. Alternatively, the light emitter may be fixed to the support and rotated together with the support.

As illustrated in FIG. 18, a light emitter 67D is formed into a circular shape around the turning axis AX1, and fixed to the inside of the support 30A. Therefore, the light emitter 67D also rotates according to the rotation of the support 30A. The light emitter 67D includes a plurality of light emitting segments that are continuously arranged into the cyclic shape. The light emission control is individually performed in each light emitting segment.

In the fifth preferred embodiment, the light emitter 67D rotates when the support 30A rotates. For example, in the case where the light emission display of the information (the center direction CD1 or the swing angle θ) about the turning is performed in the tomosynthesis photographing mode, the light emission portion is changed in synchronization with the rotation of the light emitter 67D. That is, one or at least two light emitting segments performing the light emission display move sequentially to the adjacent light emitting segment according to the turning of the support 30A.

In the above preferred embodiments, in the tomosynthesis photographing mode, the turning range of the support 30A is set by setting the center direction CD1 and the swing angle θ. Alternatively, the turning range may directly be set.

For example, as illustrated in FIG. 18, the operator manually rotates the support 30A to move the support 30A to an angle L51 at which the X-ray irradiation for the tomosynthesis photography is started. The operator performs a predetermined operation to store the angle L51 in the storage 73. Then, the operator moves the support 30A up to an angle L53 at which the X-ray irradiation is ended. The operator performs a predetermined operation to store the angle L53 in the storage 73. Thus, the turning range of the support 30A for the tomosynthesis photography is set from the angle L51 to the angle L53. The direction passing through the center of the swing angle θ from the angle L51 to the angle L53 becomes the center direction CD1. Accordingly, the operator sets the angles L51 and L53 such that the center direction CD1 is aligned with the desired visual line direction, which allows the acquisition of the good tomosynthesis image.

As to a light emission display example of the light emitter 67D, the light emitter controller 715 may cause the portion, which overlaps the X-ray axis BAX1 rotating together with the support 30A in the light emitter 67D, to sequentially emit the light when the operator rotates the support 30A from the angle L51 as illustrated in FIG. 18. That is, a portion 677a of the light emitter 67D intersecting the X-ray axis BAX1 sequentially emits the light until the support 30A rotates up to the angle L53. The plurality of light emitting segments constituting the light emitter 67D rotates together with the support 30A.

When the support 30A rotates, the light emitting segment adjacent in the opposite direction to the turning direction sequentially emits the light. Thus, the light emitting portion 677a spread along the arc of the light emitter 67. When the angles L51 and L53 are decided, the light emitter controller 715 may cause a portion 677b facing the portion 677a along the center direction CD1 to emit the light in a color different from that of the portion 677a. Thus, the light emitter 67D may perform the light emission display of the center direction CD1.

<6. Sixth Preferred Embodiment>

Figure 19:
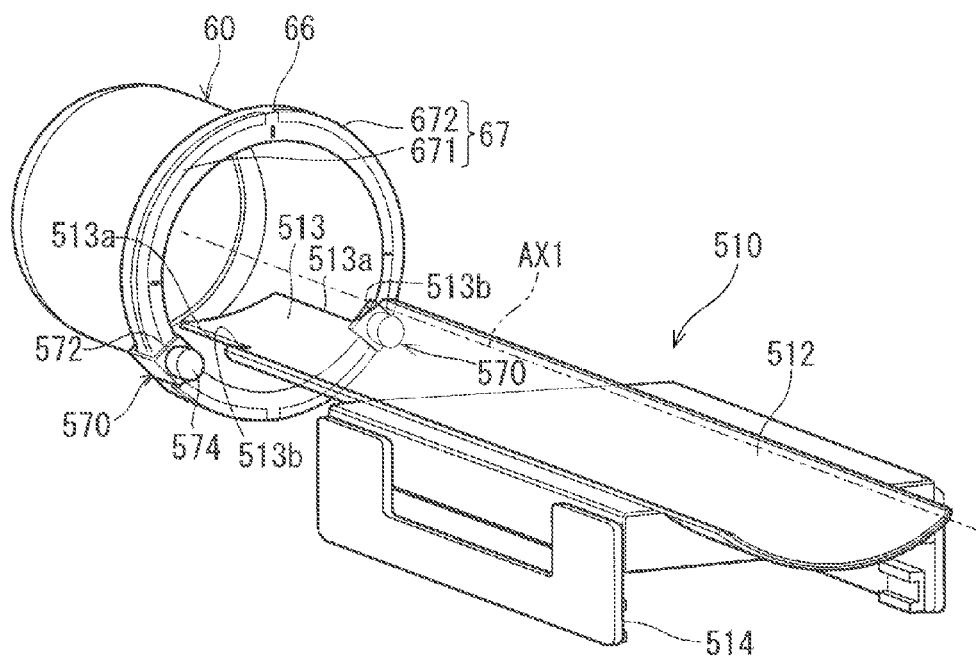
FIG. 19 is a schematic perspective view illustrating a subject holder detachably attached to a ring of an accommodation part according to a sixth preferred embodiment.
Figure 20:
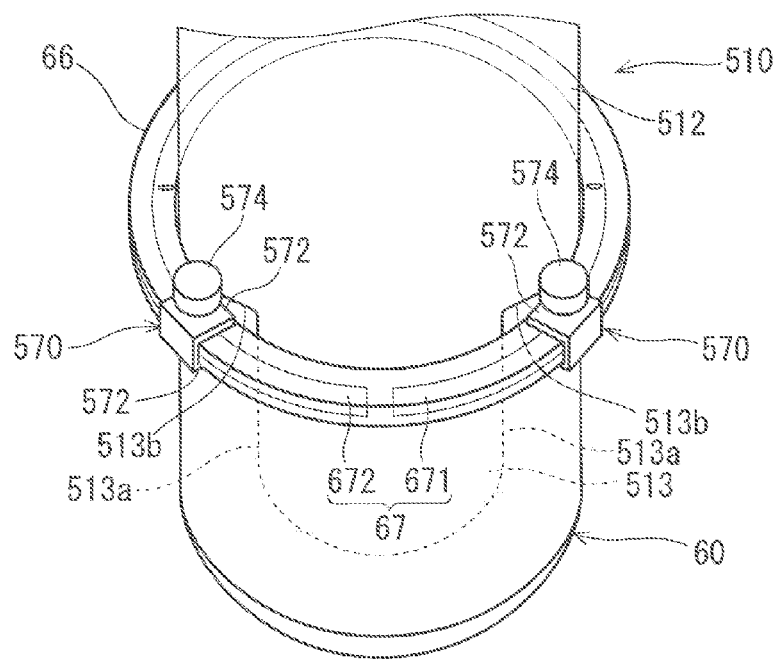
FIG. 20 is a schematic perspective view illustrating a detachably connecting part and a subject holder of the sixth preferred embodiment when the detachably connecting part and the subject holder are viewed from below.

FIG. 19 is a schematic perspective view illustrating a subject holder 510 detachably attached to a ring 66 of an accommodation part 60 according to a sixth preferred embodiment. FIG. 20 is a schematic perspective view illustrating a detachably connecting part 570 and the subject holder 510 of the sixth preferred embodiment when the detachably connecting part 570 and the subject holder 510 are viewed from below.

The subject holder 510 in FIGS. 19 and 20 is configured as a medical bed holding a whole body of the patient. The subject holder is not limited to the medical bed, but the subject holder may be a member partially holding the patient body, for example, a support stand on which an arm is placed.

The subject holder 510 includes a bed body 512 and an intermediate base 514. The bed body 512 is formed into a long shape that is recessed into an arc shape from both sides toward a central portion in a width direction. The bed body 512 has a width and a length to a degree to which the patient can be supported in a lying down state. In a one-end-side portion 513 of the bed body 512, a lateral portion associated with a body axis of the lay-down patient is cut out into a substantial L-shape in which a first side portion 513a extending along a lengthwise direction of the bed body 512 a second side portion 513b extending along a width direction of the bed body 512 are formed. The one-end-side portion 513 can be disposed inside the accommodation part 60 such that the second side portion 513b abuts on an opening portion of the accommodation part 60.

The bed body 512 is supported in a substantial horizontal attitude at a height corresponding to the accommodation part 60 by the intermediate base 514. The one-end-side portion 513 is fixed to the intermediate base 514 so as to overhang from the intermediate base 514.

In the configuration of the detachably connecting part 570, a pair of insert pieces 572 is disposed with a gap while facing each other. The gap in which the ring 66 can be disposed is provided between the pair of insert pieces 572. The ring 66 is inserted by one of the insert pieces 572, and a fixing screw 574 is driven while the detachably connecting part 570 is disposed at a desired position in a circumferential direction of the ring 564, whereby the ring 66 is held between the leading end portion of the fixing screw 574 and the other insert piece 572. Therefore, the detachably connecting part 570 is fixed to a desired position of the ring 66.

In the sixth preferred embodiment, two detachably connecting parts 570 are attached. The two detachably connecting parts 570 are fixedly attached to the ring 66 at a position, where the detachably connecting parts 570 can abut on the second side portion 513b from below, while the one-end-side portion 513 of the bed body 512 is provided in the accommodation part 60. The one-end-side portion 513 of the bed body 512 is provided in the accommodation part 60, and a lower surface portion of the second side portion 513b abuts on the detachably connecting part 570, whereby the bed body 512 is detachably coupled to the accommodation part 60. At this point, the lower surface of the second side portion 513b of the bed body 512 held in the horizontal attitude abuts on the right and left detachably connecting parts 570 and 570. Therefore, the rotation of the accommodation part 60 can more surely be regulated.

As used herein, the coupling of the accommodation part 60 and the subject holder 510 to each other means that the accommodation part 60 and the subject holder 510 are integrally connected while the rotation of the accommodation part 60 is regulated with respect to the subject holder 510. The separation of the accommodation part 60 and the subject holder 510 from each other means that a distance between the accommodation part 60 and the subject holder 510 is lengthened while the rotation regulation of the accommodation part 60 is released with respect to the subject holder 510.

Desirably, the bed body 512 of the subject holder 510 is made of a transparent material. Therefore, even if the bed body 512 is disposed between the operator and the light emitter 67, the operator can visually recognize the light emission state of the light emitter 67 over the bed body 512. Accordingly, the operator can easily set the photographing condition for the tomosynthesis photography.

<7. Seventh Preferred Embodiment>

Figure 21:
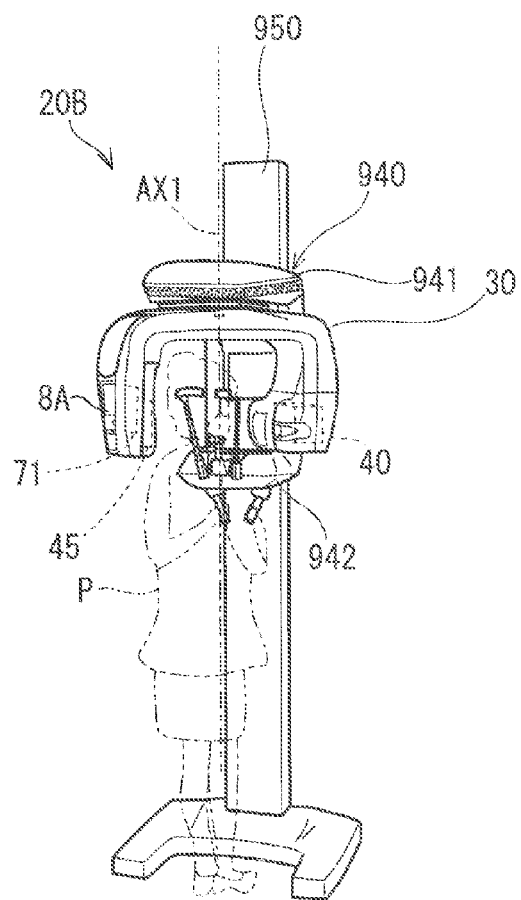
FIG. 21 is a schematic general view illustrating a medical X-ray photographing apparatus according to a seventh preferred embodiment.
Figure 22:
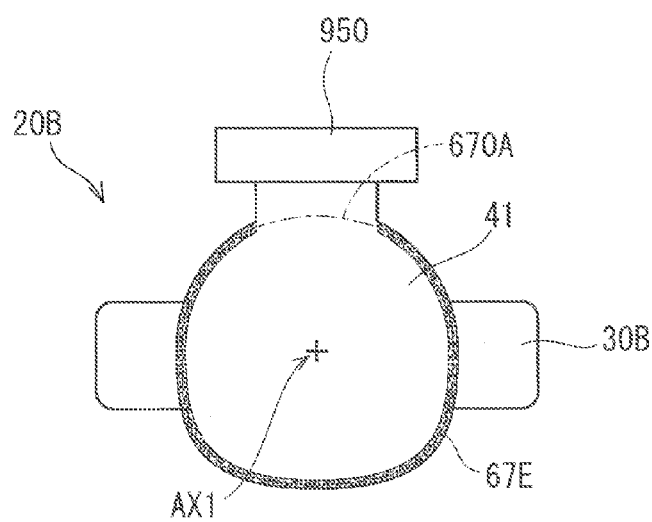
FIG. 22 is a view illustrating the medical X-ray photographing apparatus of the seventh preferred embodiment when the medical X-ray photographing apparatus is viewed from above.

FIG. 21 is a schematic general view illustrating a medical X-ray photographing apparatus 20B according to a seventh preferred embodiment. FIG. 22 is a view illustrating the medical X-ray photographing apparatus 20B of the seventh preferred embodiment when the medical X-ray photographing apparatus 20B is viewed from above. The medical X-ray photographing apparatus 20B includes a support 30B that supports the X-ray generator 40 and the X-ray detector 45 in the facing state. The support 30B is configured to turn about the turning axis AX1 extending in the vertical direction.

More particularly, the support 30B is rotatably supported in an upper frame 941 attached to a post 950. A driver (an X-direction driver and a Y-direction driver) that moves the upper frame 941 and the support 30B in the horizontal direction perpendicular to the turning axis AX1 and a turning driver that turns the support 30B about the turning axis AX1 relative to the upper frame 941 are provided in one of the upper frame 941 and the support 30B.

The upper frame 941 and the lower frame 942 are attached to the post 950, and constitute a vertical moving mechanism that is moved up and down along the vertical direction by the electric control. The upper frame 941 and the lower frame 942 move vertically to move vertically the support 30B rotatably supported in the upper frame 941.

In the medical X-ray photographing apparatus 20B, the photographing target region such as a head is disposed between the X-ray generator 40 and the X-ray detector 45 while the patient of the subject P confronts the post 950. The support 30B turns about the subject P to perform the tomosynthesis photography and the CT photography. The panoramic photography in which the X-ray photography is performed along, for example, the tooth row of the subject P or the simple X-ray photography can also be performed in the configuration of the medical X-ray photographing apparatus 20B.

In the example of FIGS. 21 and 22, the subject P provided in an upright attitude at a predetermined position while confronting the post 950. Alternatively, for example, a chair is provided, and the subject P may be provided while sitting on the chair.

In the medical X-ray photographing apparatus 20B, a light emitter 67E is provided on the virtual loop line 670A around the turning axis AX1. In the seventh preferred embodiment, the light emitter 67E is provided along the end edge of the upper frame 941. Alternatively, the light emitter 67E may be provided at another position. For example, the light emitter 67E may be provided in the lower frame 942 disposed below the support 30B.

In the configuration of the medical X-ray photographing apparatus 20B, the center direction CD1 or the swing angle θ for the tomosynthesis photography are set by the manual rotation of the support 30B or through the operating part 8A.

The light emitter controller 715 of the controller 71 causes the light emitter 67E to emit the light in association with the turning of the support 30B. Therefore, the turning condition (for example, the center direction CD1 or the turning range for the tomosynthesis photography) of the support 30B for the X-ray photography can easily be understood from the outside.

<8. Modification>

In the above preferred embodiments, the accommodation part 60 is formed into the cylindrical shape with the bottom. Alternatively, for example, the accommodation part may be formed into a shape that is opened on both sides in the axial direction or a polygonal pipe shape.

Although the present invention is described in detail above, the description is illustrative only in all aspects, but the present invention is not limited to the preferred embodiments and modification. It is noted that various modifications (not illustrated) are conceivable without departing from the scope of the present invention. The configurations described in the preferred embodiments and modification can properly be combined or omitted as long as the configurations are conflict with each other.

While the invention has been shown and described in detail, the foregoing description is in all aspects illustrative and not restrictive. It is therefore understood that numerous modifications and variations can be devised without departing from the scope of the invention.

What is claimed is:

1. A medical X-ray photographing apparatus comprising:
a support configured to turn an X-ray generator and an X-ray detector about a predetermined turning axis while holding said X-ray generator and said X-ray detector such that said X-ray generator and said X-ray detector face each other, said X-ray generator configured to emit an X-ray, said X-ray detector configured to output an electric signal according to an incident X-ray;
a support holder configured to rotatably support said support;
a motor configured to turn said support held by said support holder;
a turning controller configured to control said motor;
an image processor configured to generate an X-ray image by processing a plurality of projection images based on said electric signal;
a light emitter comprising a plurality of light emitting elements disposed on a virtual loop line surrounding said turning axis; and
a processor configured to control said light emitter in association with turning of said support, wherein
said processor controls said light emitter so that at least one of the plurality of light emitting elements acts in a way different from at least another one of the plurality of light emitting elements at least by lighting, turning off, blinking, or color, to indicate a movement of said support or a center of a swing angle of said support.

2. The medical X-ray photographing apparatus according to claim 1, wherein said light emitter is disposed on a circumference of a circle centered on said turning axis.

3. The medical X-ray photographing apparatus according to claim 2, wherein said light emitter is formed of a closed circular shape.

4. The medical X-ray photographing apparatus according to claim 1, wherein said light emitter is fixed to said support holder.

5. The medical X-ray photographing apparatus according to claim 1, wherein the plurality of light emitting elements emit light at positions separated from each other.

6. The medical X-ray photographing apparatus according to claim 1, further comprising
an angle detector configured to detect an angle of said support, wherein,
said processor, based on the detected angle of said support, lights, turns off or blinks the plurality of light emitting elements at two portions facing each other diametrically in a light emission mode, the light emission mode being different from that of other light emitting elements such that an orientation of an X-ray axis between said X-ray generator and said X-ray detector is shown.

7. The medical X-ray photographing apparatus according to claim 6, wherein when said support is turned, said processor, based on the detected angle of said support, lights, turns off or blinks at least one of the plurality of light emitting elements corresponding to a turning range of said support determined based on said detected angle in a light emission mode different from that of other light emitting elements such that the turning range of said support is shown.

8. The medical X-ray photographing apparatus according to claim 1, further comprising
an angle detector configured to detect an angle of said support, wherein,
when said support is rotated, said processor, based on the detected angle of said support, lights, turns off or blinks at least one of the plurality of light emitting elements corresponding to a turning range of said support determined based on said detected angle in a light emission mode, the light emission mode being different from that of other light emitting elements such that the turning range of said support is shown.

9. The medical X-ray photographing apparatus according to claim 1, wherein
the plurality of light emitting elements include plurality of color LEDs, and
said processor controls emission of the plurality of color LEDs according to an operating situation of said medical X-ray photographing apparatus.

10. The medical X-ray photographing apparatus according to claim 9, wherein said operating situation includes at least one of a turning preparation state of said support, on and off states of an electromagnetic lock of said support, an emergency stop state, an X-ray irradiation state, a turning angle or a turning direction of said support, and an X-ray irradiation direction.

11. The medical X-ray photographing apparatus according to claim 1, wherein said light emitter is provided at a position where said light emitter is visually recognizable from at least one of a direction along a radial direction perpendicular to said turning axis and a direction along said turning axis.

12. The medical X-ray photographing apparatus according to claim 11, wherein
said support includes an arm base having two ends, a pair of arms, each of said arms extending from each end of said arm base, and
said light emitter is provided on a side of said arm base from which said pair of arms extends.

13. The medical X-ray photographing apparatus according to claim 1, wherein said turning axis is horizontal.

14. The medical X-ray photographing apparatus according to claim 1, further comprising
a storage in which said swing angle of said support and a center direction which is a center of said swing angle in emitting the X-ray from said X-ray generator toward said X-ray detector are stored in order to perform tomosynthesis photography,
wherein said processor controls said light emitter such that said swing angle and said center direction, which are read from said storage, are indicated by said light emitter.

15. An X-ray photographing method in which X-ray photography is performed by emitting an X-ray from an X-ray generator toward an X-ray detector, said X-ray generator and said X-ray detector held in a facing state by a support, said X-ray photographing method comprising:
(a) a turning controlling step of controlling a turning of said support; and
(b) a light-emitter controlling step of controlling a light emitter including a plurality of light emitting elements, which is disposed on a virtual loop line surrounding a turning axis, in association with the turning of said support, so that at least one of the plurality of light emitting elements acts in a way different from at least another one of the plurality of light emitting elements at least by lighting, turning off, blinking, or color, to indicate a movement of said support or a center of a swing angle of said support.

16. The X-ray photographing method according to claim 15, further comprising
   (c) an angle detecting step of detecting an angle of said support, wherein,
   in said light-emitter controlling step, the light emitter at two portions facing each other diametrically is lit, turned off or blinked based on the detected angle of said support such that an orientation of an X-ray axis between said X-ray generator and said X-ray detector is shown.

17. The X-ray photographing method according to claim 16, wherein in the light-emitter controlling step, a portion of the light emitter corresponding to a turning range of said support is lit, turned off or blinked such that the turning range of said support is shown.

18. The X-ray photographing method according to claim 15, wherein in the light-emitter controlling step, a portion of the light emitter corresponding to a turning range of said support is lit, turned off or blinked such that the turning range of said support is shown.

19. A medical X-ray photographing apparatus for using the x-ray photographing method according to claim 15.

20. A medical X-ray photographing apparatus comprising:
   an X-ray generator;
   an X-ray detector, the X-ray detector for emitting an electric signal in response to receiving an X-ray beam emitted from the X-ray generator;
   an X-ray axis upon which the X-ray beam is emitted;
   a support holding the X-ray generator such that the X-ray generator faces the X-ray detector;
   an image processor for generating a tomosynthesis image based on a processing of a plurality of projection images, the plurality of projection images associated with the electric signal;
   a plurality of light emitting elements; and
   a processor for controlling the plurality of light emitting elements to visually display an orientation of the X-ray axis and for controlling the light emitting elements so that at least one of the light emitting elements acts in a way different from at least another one of the light emitting elements at least by lighting, turning off, blinking, or color, to indicate a movement of the support or a center of a swing angle of the support.

21. The medical X-ray photographing apparatus according to claim 20, wherein the processor displays a turning range of the support in coordination with a turning angle of the support.

* * * * *